(12) United States Patent
Miyoshi et al.

(10) Patent No.: US 7,678,566 B2
(45) Date of Patent: Mar. 16, 2010

(54) DEVICE FOR CHROMATOGRAPHIC QUANTITATIVE MEASUREMENT

(75) Inventors: Koji Miyoshi, Iyomishima (JP); Masahiro Aga, Ehime (JP); Kaoru Shigematsu, Ehime (JP)

(73) Assignee: Panasonic Corporation, Osaka (JP)

( * ) Notice: Subject to any disclaimer, the term of this patent is extended or adjusted under 35 U.S.C. 154(b) by 1030 days.

(21) Appl. No.: 10/148,007

(22) PCT Filed: Sep. 25, 2001

(86) PCT No.: PCT/JP01/08314

§ 371 (c)(1),
(2), (4) Date: Aug. 22, 2002

(87) PCT Pub. No.: WO02/25253

PCT Pub. Date: Mar. 28, 2002

(65) Prior Publication Data

US 2003/0054567 A1 Mar. 20, 2003

(30) Foreign Application Priority Data

Sep. 25, 2000 (JP) ............................. 2000-290952
Jun. 22, 2001 (JP) ............................. 2001-190198
Jul. 16, 2001 (JP) ............................. 2001-215745

(51) Int. Cl.
*C12M 1/34* (2006.01)

(52) U.S. Cl. ................. 435/288.7; 356/239.2; 356/300; 356/328; 356/244

(58) Field of Classification Search ................. 356/237, 356/239, 212, 210; 355/54; 435/238.1
See application file for complete search history.

(56) References Cited

U.S. PATENT DOCUMENTS

| 3,260,413 A | 7/1966 | Natelson |
| 3,556,731 A | 1/1971 | Martin |
| 3,928,203 A | 12/1975 | Kremer |

(Continued)

FOREIGN PATENT DOCUMENTS

AU 714956 1/1998

(Continued)

OTHER PUBLICATIONS

Supplementary European Search Report issued Feb. 15, 2008 in the European Application No. 01 97 0205.

(Continued)

*Primary Examiner*—N. Yang
(74) *Attorney, Agent, or Firm*—Wenderoth, Lind & Ponack L.L.P.

(57) ABSTRACT

In a chromatography quantitative measuring apparatus according to the present invention, a beam applied from a light source to a chromatography test strip is formed into an elliptical shape by an optical means such as a cylindrical lens, a variation in absorbance that accompanies elution of a marker regent is detected while the elliptical beam is applied between a marker reagent hold part and a detection part, and a measurement is automatically started in a prescribed period of time since the detection of variation. According to the chromatography quantitative measuring apparatus so configured, non-uniform coloration is reduced by shaping the beam elliptically with the optical means, whereby the accuracy of quantitative analysis is enhanced, and the apparatus can be operated easily.

4 Claims, 21 Drawing Sheets

U.S. PATENT DOCUMENTS

| | | | |
|---|---|---|---|
| 3,994,587 A | | 11/1976 | Yamamoto et al. |
| 4,072,426 A | * | 2/1978 | Horn .......................... 356/448 |
| 4,756,585 A | * | 7/1988 | Kaneko et al. .............. 359/218 |
| 4,906,439 A | | 3/1990 | Grenner |
| 4,999,285 A | | 3/1991 | Stiso |
| 5,071,746 A | * | 12/1991 | Wilk et al. ................. 435/7.94 |
| 5,132,097 A | | 7/1992 | Van Deusen et al. |
| 5,137,808 A | | 8/1992 | Ullman et al. |
| 5,225,928 A | * | 7/1993 | Dugan ........................ 359/356 |
| 5,410,400 A | * | 4/1995 | Shishido et al. .......... 356/237.4 |
| 5,530,551 A | * | 6/1996 | Cantrall et al. .............. 356/394 |
| 5,563,042 A | | 10/1996 | Phillips et al. |
| 5,569,608 A | | 10/1996 | Sommer |
| 5,673,101 A | * | 9/1997 | Tenner et al. ................. 355/53 |
| 5,753,907 A | * | 5/1998 | Nakajima et al. ........... 250/234 |
| 5,780,304 A | | 7/1998 | Matzinger et al. |
| 6,130,099 A | | 10/2000 | Kielmann |
| 2002/0004246 A1 | | 1/2002 | Daniels et al. |
| 2006/0008921 A1 | | 1/2006 | Daniels et al. |

FOREIGN PATENT DOCUMENTS

| | | |
|---|---|---|
| CN | 1146557 | 4/1997 |
| CN | 1157040 | 8/1997 |
| EP | 0 165 535 | 12/1985 |
| EP | 0323605 A2 | 7/1989 |
| EP | 0421294 A2 | 4/1991 |
| EP | 1096256 | 5/2001 |
| JP | 61-61039 | 3/1986 |
| JP | 61-109015 | 5/1986 |
| JP | 61-283186 | 12/1986 |
| JP | 62-76434 | 4/1987 |
| JP | 06276434 A | 4/1987 |
| JP | 5-332918 | 12/1993 |
| JP | 7-5110 | 1/1995 |
| JP | 7-46107 | 5/1995 |
| JP | 8-240591 | 9/1996 |
| JP | 2705767 | 10/1997 |
| JP | 10/503024 | 3/1998 |
| JP | 10-197510 | 7/1998 |
| JP | 10-274653 | 10/1998 |
| JP | 11038006 | 2/1999 |
| JP | 11-83745 | 3/1999 |
| JP | 11-142338 | 5/1999 |
| JP | 2000-507353 | 6/2000 |
| JP | 2001-296246 | 10/2001 |
| WO | 94/22011 | 9/1994 |
| WO | 96/09553 | 3/1996 |
| WO | 01/57522 A2 | 8/2001 |

OTHER PUBLICATIONS

European Search Report issued Oct. 7, 2009 in corresponding Application No. 09158427.6.

* cited by examiner

US 7,678,566 B2

DEVICE FOR CHROMATOGRAPHIC QUANTITATIVE MEASUREMENT

This application is the national stage of PCT/JP01/08314, filed Sep. 25, 2001, which in turn claims foreign priority to foreign applications Japan 2000290952, filed Sep. 25, 2000, Japan 2001190198, filed Jun. 22, 2001, and Japan 2001215745, filed Jul. 16, 2001.

TECHNICAL FIELD

The present invention relates to a chromatography quantitative measuring apparatus which performs a measurement employing an immuno-chromatography test strip or the like, and more particularly, to one which is improved in performing a quantitative measurement.

BACKGROUND ART

Hereinafter, a description will be given of a spectrophotometer as a conventional chromatography quantitative measuring apparatus. FIG. 25(a) is a diagram schematically illustrating the configuration of the conventional reflective spectrophotometer, and FIG. 25(b) is a diagram illustrating the constitution of a chromatography test strip.

In FIG. 25(a), an optical beam 11 emitted from a lamp 1 is input to a diffraction grating 3 via a reflector 2. The optical beam 11 input to the diffraction grating 3 is selected thereby for its light wavelength, and the optical beam 11 is narrowed by an aperture 4 and input to a glass plate 5. The optical beam 11 reflected at the glass plate 5 is received by a first photomultiplier tube 7 as a reference beam 6. On the other hand, the optical beam 11 transmitted through the glass plate 5 is applied to a part of a chromatography test strip 8, and a scattering light 9 from the chromatography test strip 8 is received by a second photomultiplier tube 10. Output signals from the first photomultiplier tube 7 and the second photomultiplier tube 10 are respectively subjected to Log transformation, and a value obtained by subtracting a Log transformed value for the second photomultiplier tube 10 from a Log transformed value for the first photomultiplier tube 7 is output as an absorbance signal.

As shown in FIG. 25(b), the immuno-chromatography test strip 8 utilizing an antigen antibody reaction comprises an application part 81 where a liquid sample as an inspection target solution is applied, a marker reagent hold part 82 which holds a marker reagent which is moved by permeation of the liquid sample and has a substance that is specifically bounded to an analysis target included in the liquid which flows therein, a detection part 83 where the marker reagent and the analysis target are bounded and immobilized, a part for absorbing the sample which flows therein, and a remaining base part 84.

An operation of the so-configured chromatography quantitative measuring apparatus will be described.

First, when an inspection target solution is applied to the application part 81, the inspection target solution is developed on a development layer 85. At this time, when the inspection target solution reaches the marker reagent hold part 82, a marker reagent is eluted and specifically bonded to an analysis target included in the inspection target solution. Then, this bounded material is immobilized at the detection part 83, and a non-immobilized residual marker reagent flows downstream of the development layer 85 without being immobilized.

Next, as shown in FIG. 25(a), a beam is applied to the chromatography test strip 8 from the light source 1 so as to measure the concentration of the analysis target included in the inspection target solution. A previously-calculated calibration curve indicates a relationship between the difference between the absorbance signal at the base part 84 of the chromatography test strip 8 and the absorbance signal at the detection part 83, and the concentration of a sample to be measured. The concentration of the sample is calculated by detecting the difference between the absorbance signal at the base part 84 and that at the detection part 83.

While analysis by immuno-chromatography is generally qualitative, a method of quantitative analysis has also been developed. For example, Japanese Published Patent Application No. Hei. 8-240591 discloses a method by which the degree of coloration is quantitatively measured by measuring signals of absorbance, reflection, and the like at a coloration part on a test strip employing a spectrophotometer after a sample is applied to the immuno-chromatography test strip and a reaction is caused thereon. Further, Japanese Published Patent Application No. Hei. 11-142338 discloses a method by which the absorbance at the coloration part is measured without influence of outside light by using a light emitting diode as a light source.

However, in the conventional chromatography quantitative measuring apparatus, which has no problem with respect to immuno-chromatography for qualitative analysis, in the case of quantitative analysis, when, for example, a liquid sample including cellular components, such as blood, is to be analyzed, the viscosity of the liquid sample or the existence of cellular components generates partial clogging, resulting in non-uniform coloration at the base part of the immuno-chromatography test strip. Thus, as the concentration is obtained by the difference between the absorbance signal at the base part and that at the detection part, when an error is generated due to the non-uniform coloration at the base part according to the position where a beam is applied, a quantitative measurement is disturbed. Further, when a spectrophotometer which uses a lamp as a light source is used, it is difficult to reduce the size and cost of the apparatus.

Further, in the above-described conventional chromatography quantitative measuring apparatus, since the inspection target solution is slowly developed on the development layer 85, a value of a detection signal is gradually varied with time at the detection part 83 of the chromatography test strip 8. That is, in order to obtain a more stable measurement result, it is important to manage time to perform a measurement. In the conventional measurement using a spectrophotometer, there is no function of managing time, and as a result, an inspector has to manage time manually, which causes trouble in a measurement operation. Further, there is sometimes a test strip on which a normal measurement is disturbed according to the inspection target solution or a state of the chromatography test strip 8. In the conventional measurement using a spectrophotometer, there is no function of detecting the state of the inspection target solution or the chromatography test strip 8, and as a result, an inspector has to judge the state manually, which causes trouble in a measurement operation. Furthermore, since a marker reagent remains at the marker reagent hold part 82 of the chromatography test strip 8 even after its elution, influences of the residual marker reagent must be reduced in order to enhance the accuracy of a quantitative measurement. However, in the conventional measurement using a spectrophotometer, there is no function of recognizing the residual marker reagent, and as a result, an inspector has to recognize it manually, which causes trouble in a measurement operation.

Further, an immuno-chromatography test strip for a qualitative or semi-quantitative measurement is generally put in a hollow casing and discarded together with the casing when an inspection is ended. For example, in Japanese Published Patent Applications No. Hei. 1-503174 and No. Hei. 6-180320, methods are disclosed in which a casing 90 with an injection part 91 through which a liquid sample is applied to the immuno-chromatography test strip, and an aperture 92 for observing a coloration part are provided, and the degree of coloration is visually judged as an inspection result, as shown in FIG. 25(*c*). Further, in immuno-chromatography quantitative analysis for measuring the degree of coloration by a multi-purpose spectrophotometer, there is no problem in employing the casing when the frequency of measurements is low. However, when a quantitative measurement is performed frequently for the purpose of clinical examination or the like, there is a problem of the cost of the casing and a storage space to be secured. On the other hand, when the quantitative measurement is performed by solely employing the immuno-chromatography test strip without the casing, the test strip is put on a measurement table of the spectrophotometer directly, so that a sample adheres to a measuring apparatus. Furthermore, the test strip must be attached to the measuring apparatus precisely so that a beam is accurately applied to the base part and the detection part.

The present invention is made to solve the above-mentioned problems. Accordingly, an object of the present invention is to provide a chromatography quantitative measuring apparatus which makes highly accurate immuno-chromatography quantitative analysis possible and realizes a reduction in the size and cost of the apparatus, a chromatography quantitative measuring apparatus which improves operationality thereof, or a chromatography quantitative measuring apparatus which enhances the accuracy of a quantitative measurement.

SUMMARY OF THE INVENTION

According to a first aspect of the present invention, a chromatography quantitative measuring apparatus is provided which applies a beam emitted from a light source to a sample, detects an optical signal from a transmitted light or reflected light from the sample, and quantitatively reads the concentration of the sample from the signal. The chromatography quantitative measuring apparatus includes an optical means for forming the beam emitted from the light source into an elliptical or rectangular shape and applying the elliptically or rectangularly shaped beam to the sample.

Therefore, it is possible to perform a quantitative measurement with fewer measurement errors which are caused by non-uniform coloration at a base part.

According to a second aspect of the present invention, in accordance with the chromatography quantitative measuring apparatus of the first aspect, the sample is put on an immuno-chromatography test strip, and the beam applied to the sample has a longer side which is shorter than the width of the immuno-chromatography test strip in the width direction that is orthogonal with respect to the long-side direction.

Therefore, it is possible to perform a quantitative measurement with much fewer measurement errors which are caused by non-uniform coloration at a base part.

According to a third aspect of the present invention, in accordance with the chromatography quantitative measuring apparatus of the first aspect, the sample is put on an immuno-chromatography test strip, and the beam applied to the sample has a shorter side which is shorter than the width of a detection part region of the immuno-chromatography test strip.

Therefore, it is possible to perform a quantitative measurement with much fewer measurement errors which are caused by non-uniform coloration at a base part.

According to a fourth aspect of the present invention, in accordance with the chromatography quantitative measuring apparatus of any one of the first to third aspects, the optical signal is detected by scanning the beam applied to the sample, or the sample.

Therefore, an operation for measuring a difference between absorbance signals is simplified, resulting in an effective measurement.

According to a fifth aspect of the present invention, in accordance with the chromatography quantitative measuring apparatus of the first aspect, a laser is used as the light source, and a laser beam from the light source is converted into a collimated beam via a collimator lens. Further, the optical means forms the collimated beam into an elliptical shape via a cylindrical lens and applies the elliptically shaped beam to the sample.

Therefore, the size of the apparatus can be reduced by employing a laser as a light source, and since a measurement is sufficiently performed with a photodiode, as compared with a conventional sample concentration measuring apparatus which uses a photomultiplier tube to receive a scattering light and a reflected light from a sample, the cost of the apparatus can be reduced.

According to a sixth aspect of the present invention, in accordance with the chromatography quantitative measuring apparatus of the first aspect, a laser is used as the light source, and the laser beam from the light source is converted into a collimated beam via a collimator lens. Further, the optical means forms the collimated beam into a rectangular shape via a rectangularly shaped aperture member and applies the rectangularly shaped beam to the sample. Therefore, the size of the apparatus can be reduced by employing a laser as a light source, and since a measurement is sufficiently performed with a photodiode, as compared with a conventional apparatus using a photomultiplier tube to receive a scattering light and a reflected light from a sample, the cost of the apparatus can be reduced.

According to a seventh aspect of the present invention, a chromatography quantitative measuring apparatus is provided which applies a beam emitted from a light source to a sample, detects an optical signal from a transmitted light or reflected light from the sample, and quantitatively reads the concentration of the sample from the signal. The chromatography quantitative measuring apparatus includes a laser as the light source, and a collimator lens which converts the laser beam into a collimated beam. In the chromatography quantitative measuring apparatus, when the collimated beam is shaped rectangularly via an aperture member and the rectangularly shaped beam is applied to the sample, the direction of a longer side of the rectangularly shaped beam is made to correspond to the direction in which the beam divergence angle of the laser becomes larger.

Therefore, it is possible to perform a quantitative measurement with much fewer measurement errors.

According to an eighth aspect of the present invention, a chromatography quantitative measuring apparatus is provided which applies a beam emitted from a light source to a sample, detects an optical signal from a transmitted light or reflected light from the sample, and quantitatively reads the concentration of the sample from the signal. The chromatography quantitative measuring apparatus includes a laser as the light source, and a collimator lens which converts the laser beam into a collimated beam. In the chromatography quantitative measuring apparatus when the collimated beam is shaped elliptically via a cylindrical lens and the elliptically shaped beam is applied to the sample, the direction of a longer side of the elliptically shaped beam is made to correspond to the direction in which the beam divergence angle of the laser becomes larger.

Therefore, it is possible to perform a quantitative measurement with much fewer measurement errors.

According to a ninth aspect of the present invention, the chromatography quantitative measuring apparatus of any one of the fifth to eighth aspects includes a compensation means for storing the initial wavelength of the laser, calculating the present wavelength of the laser to compensate by the provision of a temperature detection element in the vicinity of the laser, and compensating an optical signal detection value or the converted concentration of the sample which is obtained by converting the optical signal detection value.

Therefore, it is possible to perform a quantitative measurement with fewer measurement errors by reducing an influence of a hardware configuration or usage environment.

According to a tenth aspect of the present invention, in accordance with the chromatography quantitative measuring apparatus of the ninth aspect, the compensation means performs processing for detecting the optical signal, processing for obtaining the converted concentration of the sample, and processing for compensating the converted concentration, with the same calculator.

Therefore, it is possible to reduce the size of the apparatus.

According to an eleventh aspect of the present invention, in accordance with the chromatography quantitative measuring apparatus of any one of the fifth to eighth aspects, the concentration of the sample is calculated from a difference between electronic signals obtained by two light receiving elements, i.e., a reference beam light receiving element which receives a reference beam separated from the beam emitted from the laser, and a scattering light receiving element which receives a scattering light generated by the application of the laser to the sample. Further, the area of the reference beam light receiving element for receiving light is smaller than the area of the scattering light receiving element for receiving light.

Therefore, it is possible to reduce the cost and size of the apparatus.

According to a twelfth aspect of the present invention, in accordance with the chromatography quantitative measuring apparatus of any one of the fifth to eighth aspects, the concentration of the sample is calculated from a difference between electronic signals obtained by two light receiving elements, i.e., a reference beam light receiving element which receives a reference beam separated from the beam emitted from the laser, and a scattering light receiving element which receives a scattering light generated by the application of the laser to the sample. Further, this chromatography quantitative measuring apparatus includes a condensing means for condensing the scattering light from the sample on the scattering light receiving element.

Therefore, it is possible to reduce the size of the scattering light receiving element, thereby reducing the cost and size of the apparatus.

According to a thirteenth aspect of the present invention, in accordance with the chromatography quantitative measuring apparatus of the twelfth aspect, the condensing means is a concave mirror which condenses a light from the sample that is scattered in the opposite direction of the direction in which the scattering light receiving element is arranged, on the scattering light receiving element.

Therefore, it is possible to reduce the size of the scattering light receiving element, thereby reducing the cost of the apparatus.

According to a fourteenth aspect of the present invention, in accordance with the chromatography quantitative measuring apparatus of the twelfth aspect, the condensing means is a condensing lens arranged between the sample and the scattering light receiving element, which condenses the scattering light from the sample that goes toward the scattering light receiving element, on the scattering light receiving element.

Therefore, it is possible to reduce the size of the scattering light receiving element, thereby reducing the cost of the apparatus.

According to a fifteenth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measuring apparatus detects an optical signal by utilizing a transmitted light or reflected light from the chromatography test strip, and quantitatively measures the concentration of the analysis target included in the inspection target solution from the signal. In which the chromatography quantitative measuring apparatus, the inspection target solution is applied to the chromatography test strip, the optical beam is applied to a prescribed position of the base part, a variation of the transmitted light or reflected light from the chromatography test strip, which is generated by the elution of the marker reagent that accompanies the development of the inspection target solution, is detected, and the concentration of the analysis target included in the inspection target solution is measured in a prescribed period of time since the detection of variation.

Therefore, an operator does not need to manage time manually, and because a measurement is performed after the elution of the marker reagent is detected, it is possible to discriminate a used test strip where a marker reagent is already eluted.

According to a sixteenth aspect of the present invention, in accordance with the chromatography quantitative measuring apparatus of the fifteenth aspect, at least one of temperature and humidity is monitored, and a previously set prescribed period of time after which the measurement of the concentration of the analysis target is performed is compensated.

Therefore, it is possible to reduce the influence of surrounding temperature and humidity on a variation in speed of development of the inspection target solution on the chromatography test strip.

According to a seventeenth aspect of the present invention, in accordance with the chromatography quantitative measuring apparatus of the fifteenth aspect, the light source is repeatedly lighted and extinguished alternately while the development of the inspection target solution is detected.

Therefore, it is possible to prevent deterioration in the performance of the chromatography test strip, which accompanies a temperature rise at a part for applying a laser beam to the chromatography test strip.

According to an eighteenth aspect of the present invention, in accordance with the chromatography quantitative measuring apparatus of the fifteenth aspect, the light source is extinguished until shortly before the detection of the development of the inspection target solution.

Therefore, it is possible to prevent deterioration in the performance of the chromatography test strip, which accompanies a temperature rise at a part for applying a laser beam to the chromatography test strip.

According to a nineteenth aspect of the present invention, in accordance with the chromatography quantitative measuring apparatus of the fifteenth aspect, output from the light source is set lower than that when the concentration of the analysis target is measured, while the development of the inspection target solution is detected.

Therefore, it is possible to prevent deterioration in the performance of the chromatography test strip, which accompanies a temperature rise at a part for applying a laser beam to the chromatography test strip.

According to a twentieth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measuring apparatus detects an optical signal by utilizing a transmitted light or reflected light from the chromatography test strip, and quantitatively measures the concentration of the analysis target included in the inspection target solution from the signal. In which the chromatography quantitative measuring apparatus, the inspection target solution is applied to the chromatography test strip, a speed of development after the application of the inspection target solution is detected, and it is judged whether performance of the chromatography test strip is high or low from the speed of development.

Therefore, it is possible to judge whether or not there is a defect on the chromatography test strip such as abnormal clogging.

According to a twenty-first aspect of the present invention, in accordance with the chromatography quantitative measuring apparatus of the twentieth aspect, the speed of development is calculated by detecting time variation of value of a detection signal, which is generated by the flow of the marker reagent that accompanies the development of the inspection target solution on the chromatography test strip.

Therefore, it is possible to judge whether or not there is a defect on the chromatography test strip such as abnormal clogging.

According to a twenty-second aspect of the present invention, in accordance with the chromatography quantitative measuring apparatus of the twentieth aspect, the speed of development is calculated from a speed of scanning of the optical beam, when the optical beam is scanned so that a value of the detection signal, which is generated by the elution of the marker reagent that accompanies the development of the inspection target solution on the chromatography test strip, is kept constant.

Therefore, it is possible to judge whether or not there is a defect on the chromatography test strip such as abnormal clogging.

According to twenty-third aspect of the present invention, in accordance with the chromatography quantitative measuring apparatus of the twentieth aspect, a discrimination value of the speed of development, from which whether performance of the chromatography test strip is high or low is judged, is compensated from a result of measuring at least one of surrounding temperature and humidity at the development of the inspection target solution on the chromatography test strip.

Therefore, it is possible to prevent an erroneous judgement as to whether performance is high or low, which is due to influence of temperature or humidity.

According to a twenty-fourth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measuring apparatus detects an optical signal by utilizing a transmitted light or reflected light from the chromatography test strip, and quantitatively measures the concentration of the analysis target included in the inspection target solution from the signal. In which the chromatography quantitative measuring apparatus, a kind of inspection target solution is judged from a detection signal at the base part on the chromatography test strip where the inspection target solution is applied.

Therefore, it is possible to judge a kind of inspection target solution which is applied to the chromatography test strip.

According to a twenty-fifth aspect of the present invention, in accordance with the chromatography quantitative measuring apparatus of the twenty-fourth aspect, the base part where the detection signal is measured is located downstream of the detection part in the direction of the development.

Therefore, it is possible to suppress an erroneous judgement on a kind of inspection target solution, which is due to influences of a marker reagent that is liable to remain at a base part upstream of the detection part as compared with a base part downstream thereof.

According to a twenty-sixth aspect of the present invention, in accordance with the chromatography quantitative measuring apparatus of the twenty-fourth aspect, a calibration curve in conformity with the inspection target solution can be selected previously.

Therefore, when plural kinds of inspection target solutions are measured, an operator does not need to manually input a kind of inspection target solution to the apparatus, resulting in an automatic measurement.

According to a twenty-seventh aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measurement apparatus detects an optical signal by utilizing a transmitted light or reflected light from the chromatography test strip, and quantitatively measures the concentration of the analysis target included in the inspection target solution from the signal. In which the chromatography quantitative measuring apparatus, a deficiency in the amount of inspection target solution applied and insufficient development on the chromatography test strip are judged from a detection signal that is obtained by applying the optical beam to the downstream end part of the base part on the chromatography test strip where the inspection target solution is applied.

Therefore, it is possible to detect a deficiency in the amount of inspection target solution applied to the chromatography test strip, or an insufficient development on the chromatography test strip which is generated by clogging or the like.

According to a twenty-eighth aspect of the present invention, in accordance with the chromatography quantitative measuring apparatus of the twenty-seventh aspect, the optical beam is scanned from the upstream end part of the base part on the chromatography test strip to the downstream end part thereof.

Therefore, no new light source is required to detect a deficiency in the amount of inspection target solution applied and an insufficient development on the chromatography test strip, thereby restraining increase in the size and cost of the apparatus that accompany addition of the function.

According to a twenty-ninth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measuring apparatus, detects an optical signal by utilizing a transmitted light or reflected light from the chromatography test strip, and quantitatively measures the concentration of the analysis target included in the inspection target solution from the signal. In which the chromatography quantitative measuring apparatus, when a detection signal at a part downstream of the detection part in the direction of the development, where influence of the detection part is not exerted, is a standard value, a detection signal at the detection part is taken as a detection signal for the measurement of concentration.

Therefore, it is possible to suppress influence of an error in a measurement of absorbance, which is due to a marker reagent liable to remain at a base part upstream of the detection part as compared with a base part downstream thereof.

According to a thirtieth aspect of the present invention, in accordance with the chromatography quantitative measuring apparatus of the twenty-ninth aspect, the detection signal for the measurement of concentration is an average value of values about an extreme value of the detection part, and the detection signal as the standard value is an average value of values in the vicinity of the position downstream of the detection part in the direction in which the inspection target solution is developed, where influence of the detection part is not exerted.

Therefore, even when an electrical noise is accidentally added to the detection signal, it is possible to reduce influence on the result of calculation for obtaining the concentration of an analysis target.

According to a thirty-first aspect of the present invention, in accordance with the chromatography quantitative measuring apparatus of the twenty-ninth aspect, the detection signal for the measurement of concentration is an intermediate value of values about an extreme value of the detection part, and the detection signal as the standard value is an intermediate value of values in the vicinity of the position downstream of the detection part in the direction in which the inspection target solution is developed, where influence of the detection part is not exerted.

Therefore, even when an electrical noise is accidentally added to the detection signal, an influence on the result of calculation for obtaining the concentration of an analysis target can be reduced further as compared with a case when an average value is employed.

According to a thirty-second aspect of the present invention, in accordance with the chromatography quantitative measuring apparatus of the twenty-ninth aspect, a comparison is made of values about an extreme value of the detection signal at the detection part, and when a difference therebetween exceeds a discrimination value, the chromatography test strip is judged to be low in performance.

Therefore, it is possible to avoid an erroneous measurement due to non-uniform immobilization of a marker reagent at the detection part, a flaw on the surface of the chromatography test strip, or the like.

According to a thirty-third aspect of the present invention, in accordance with the chromatography quantitative measuring apparatus of the twenty-ninth aspect, a comparison is made of values in the vicinity of a position downstream of the detection part in the direction of the development, where influence of the detection part is not exerted, and when a difference therebetween exceeds a discrimination value, the chromatography test strip is judged to be low in performance.

Therefore, it is possible to avoid an erroneous measurement due to non-uniform development of the inspection target solution at the base part by clogging, a flaw on the surface of the chromatography test strip, or the like.

According to a thirty-fourth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measurement apparatus detects an optical signal utilizing a transmitted light or reflected light from the chromatography test strip, and quantitatively measures the concentration of the analysis target included in the inspection target solution from the signal. In which the chromatography quantitative measuring apparatus, the measurement of concentration is performed on the chromatography test strip exclusive of the marker reagent hold part.

Therefore, a measured value of absorbance at the marker reagent hold part is not included, whereby an erroneous recognition of the peak position of the absorbance is prevented, resulting in a normal detection of the concentration of an analysis target.

According to a thirty-fifth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measurement apparatus detects an optical signal utilizing a transmitted light or reflected light from the chromatography test strip, and quantitatively measures the concentration of the analysis target included in the inspection target solution from the signal. In which the chromatography quantitative measuring apparatus, a region on the chromatography test strip where a value of the detection signal is flat is taken as a region of the marker reagent hold part.

Therefore, an erroneous recognition of the peak position of the absorbance is prevented, resulting in a normal detection of the concentration of an analysis target.

According to a thirty-sixth aspect of the present invention, in accordance with the chromatography quantitative measuring apparatus of the thirty-fifth aspect, the width of the region on the chromatography test strip where the value of the detection signal is flat is calculated, and the width is compared with a prescribed width of the marker reagent hold part.

Therefore, the amount of marker reagent held can be confirmed, whereby it is possible to judge whether or not the chromatography test strip is low in performance.

According to a thirty-seventh aspect of the present invention, in accordance with the chromatography quantitative measuring apparatus of the thirty-fifth aspect, a value in the region on the chromatography test strip where the detection signal is flat is detected, and the amount of residual marker reagent is confirmed from the detected value.

Therefore, it is possible to confirm whether or not the marker reagent has flown normally.

According to a thirty-eighth aspect of the present invention, a chromatography quantitative measuring apparatus is provided which applies an optical beam emitted from a light source to a chromatography test strip that comprises an application part where an inspection target solution is applied, a marker reagent hold part which holds a marker reagent that can be eluted by development of the inspection target solution, a base part where a specific binding reaction is caused between the marker reagent and an analysis target included in the inspection target solution, and a detection part where a bounded material of the marker reagent and the analysis target is immobilized. The chromatography quantitative measurement apparatus detects an optical signal utilizing a transmitted light or reflected light from the chromatography test strip, and quantitatively measures the concentration of the analysis target included in the inspection target solution from the signal. In which the chromatography quantitative measuring apparatus, a rise and fall of a detection signal are recognized, and an extreme value of the detection signal is obtained.

Therefore, an erroneous recognition of the peak position of the absorbance is prevented, resulting in a normal detection of the concentration of an analysis target.

According to a thirty-ninth aspect of the present invention, in accordance with the chromatography quantitative measuring apparatus of the thirty-eighth aspect, the rise and fall of the detection signal is recognized, an interval between the rise and the fall is calculated, and the size of the interval is compared with a prescribed width of the detection part.

Therefore, the width of the detection part can be confirmed, whereby it is possible to judge whether or not the chromatography test strip is low in performance.

According to a fortieth aspect of the present invention, a chromatography quantitative measuring apparatus is provided for performing a quantitative measurement by applying an inspection target solution to an immuno-chromatography test strip, applying a beam to a detection part of the immuno-chromatography test strip after development of the inspection target solution, so as to detect an optical signal, and quantitatively reading the concentration of a sample from the detected signal. The chromatography quantitative measuring apparatus includes a fixing table for holding the immuno-chromatography test strip and a measurement table for holding the fixing table, in which the immuno-chromatography test strip comprises a development layer for developing the inspection target solution and a carrier for holding the development layer.

Therefore, the immuno-chromatography test strip can be accurately attached to the chromatography quantitative measuring apparatus, and it is possible to reduce the cost for a casing and a storage space.

According to a forty-first of the present invention, in accordance with the chromatography quantitative measuring apparatus of the fortieth aspect, the measurement table is provided with a groove for positioning the fixing table.

Therefore, the fixing table can be accurately attached to the measurement table.

According to a forty-second aspect of the present invention, in accordance with the chromatography quantitative measuring apparatus as defined in the fortieth aspect, the measurement table is provided with a movable projection for fixing the fixing table.

Therefore, the fixing table can be accurately attached to the measurement table.

According to a forty-third aspect of the present invention, in accordance with the chromatography quantitative measuring apparatus of the fortieth aspect, the quantitative measurement is performed by scanning the beam.

Therefore, an absorbance signal at both of the base part and the detection part of the immuno-chromatography test strip can be obtained.

According to a forty-fourth aspect of the present invention, in accordance with the chromatography quantitative measuring apparatus of the fortieth aspect, the fixing table is provided with a projection, and the carrier is provided with a hole in which the projection can be inserted.

Therefore, the immuno-chromatography test strip can be positioned on the fixing table and attached thereto.

According to a forty-fifth aspect of the present invention, in accordance with the chromatography quantitative measuring apparatus of the forty-fourth aspect, the hole has a round shape.

Therefore, the immuno-chromatography test strip can be positioned on the fixing table and attached thereto.

According to a forty-sixth aspect of the present invention, in accordance with the chromatography quantitative measuring apparatus of the forty-fourth aspect, the hole has a rectangular shape.

Therefore, the immuno-chromatography test strip can be positioned on the fixing table and attached thereto.

According to a forty-seventh aspect of the present invention, in accordance with the chromatography quantitative measuring apparatus of the forty-fourth aspect, the hole is provided downstream of the development layer in the direction in which the inspection target solution is developed.

Therefore, a sample is prevented from adhering to the fixing table.

According to a forty-eighth aspect of the present invention, in accordance with the chromatography quantitative measuring apparatus of the forty-fourth aspect, the hole is provided asymmetrically with respect to the center line of the immuno-chromatography test strip in the longer-side direction.

Therefore, the immuno-chromatography test strip is prevented from being attached to the fixing table inside out.

According to a forty-ninth aspect of the present invention, in accordance with the chromatography quantitative measuring apparatus of the fortieth aspect, the fixing table is provided with a guide, and the carrier is larger than the development layer and follows the shape of the guide.

Therefore, the immuno-chromatography test strip can be accurately attached to the fixing table without the development layer adhering to the guide.

According to a fiftieth aspect of the present invention, in accordance with the chromatography quantitative measuring apparatus of the forty-ninth aspect, a part of the guide is inclined.

Therefore, the carrier can easily follow the shape of the guide.

According to a fifty-first aspect of the present invention, in accordance with the chromatography quantitative measuring apparatus of the forty-ninth aspect, the carrier is provided with a notch in which the guide can be inserted.

Therefore, the immuno-chromatography test strip can be accurately attached to the fixing table without the development layer adhering to the guide.

According to a fifty-second aspect of the present invention, in accordance with the chromatography quantitative measuring apparatus of the fortieth aspect, the measurement table is provided with a projection, and the immuno-chromatography test strip and the fixing table are provided with holes in which the projection can be inserted.

Therefore, the immuno-chromatography test strip can be easily attached to the fixing table, and be accurately attached to the measurement table.

According to a fifty-third aspect of the present invention, in accordance with the chromatography quantitative measuring apparatus of the fifty-second aspect, the projection has its end inclined.

Therefore, the immuno-chromatography test strip can be attached more easily.

According to a fifty-fourth aspect of the present invention, the chromatography quantitative measuring apparatus of the fortieth aspect includes a test strip fixing device for fixing the immuno-chromatography test strip on the fixing table, in which the test strip fixing device presses the vicinity of a measurement area of the immuno-chromatography test strip.

Therefore, a part of the immuno-chromatography test strip where a beam is applied can be smoothed.

According to a fifty-fifth aspect of the present invention, in accordance with the chromatography quantitative measuring apparatus of the fifty-fourth aspect, the test strip fixing device presses the carrier of the immuno-chromatography test strip.

Therefore, a part of the immuno-chromatography test strip where a beam is applied can be smoothed without the development layer adhering to the test strip fixing device.

According to a fifty-sixth aspect of the present invention, in accordance with the chromatography quantitative measuring apparatus the fifty-fourth aspect, the test strip fixing device is provided with a transmission window through which the beam is transmitted.

Therefore, a measurement operation can be performed while the test strip fixing device is attached.

According to a fifty-seventh aspect of the present invention, in accordance with the chromatography quantitative measuring apparatus of the fifty-fourth aspect, the test strip fixing device is provided with pawl-shaped projections for fixing the test strip fixing device on the fixing table.

Therefore, the test strip fixing device can be easily attached.

According to a fifty-eighth aspect of the present invention, in accordance with the chromatography quantitative measuring apparatus of the fifty-fourth aspect, the test strip fixing device slides along the fixing table.

Therefore, the test strip fixing device can be easily attached.

According to a fifty-ninth aspect of the present invention, in accordance with the chromatography quantitative measuring apparatus of the fifty-eighth aspect, the test strip fixing device or the fixing table is provided with an inclination part, and the test strip fixing device and the fixing table are brought into contact at the inclination part, thereby fixing the test strip fixing device on the fixing table.

Therefore, the test strip fixing device can be easily fixed on the fixing table.

According to a sixtieth aspect of the present invention, in accordance with the chromatography quantitative measuring apparatus of the fifty-fourth aspect, the test strip fixing device is integrated with the fixing table.

Therefore, it is possible to prevent a loss of the test strip fixing device.

According to a sixty-first aspect of the present invention, in accordance with the chromatography quantitative measuring apparatus of the fifty-fourth aspect, the test strip fixing device is provided with handles.

Therefore, the test strip fixing device is easy to deal with.

According to a sixty-second aspect of the present invention, in accordance with the chromatography quantitative measuring apparatus of the fifty-fourth aspect, the test strip fixing device is provided with a needle which penetrates the immuno-chromatography test strip.

Therefore, the immuno-chromatography test strip can be easily removed from the fixing table.

According to a sixty-third aspect of the present invention, in accordance with the chromatography quantitative measuring apparatus of the fortieth aspect, the carrier is provided with grooves, and the fixing table or the measurement table is provided with a guide which can be inserted in the grooves.

Therefore, the immuno-chromatography test strip can be accurately attached to the fixing table without the development layer adhering to the guide.

According to a sixty-fourth aspect of the present invention, in accordance with the chromatography quantitative measuring apparatus of the sixty-third aspect, the grooves are formed by a laser cutter.

Therefore, the process of manufacturing the immuno-chromatography test strip can be simplified.

According to a sixty-fifth aspect of the present invention, in accordance with the chromatography quantitative measuring apparatus of the fortieth aspect, the fixing table is provided with an insertion slot in which the immuno-chromatography test strip can be inserted.

Therefore, the immuno-chromatography test strip can be easily attached to the fixing table.

According to a sixty-sixth aspect of the present invention, in accordance with the chromatography quantitative measuring apparatus of the sixty-fifth aspect, the insertion slot is inclined.

Therefore, the immuno-chromatography test strip can be easily inserted in the fixing table.

According to a sixty-seventh aspect of the present invention, in accordance with the chromatography quantitative measuring apparatus of the sixty-fifth aspect, the immuno-chromatography test strip is provided with a notch at its end on the side of insertion into the fixing table, and the fixing table is provided with a projection which has the shape same as that of the notch.

Therefore, the immuno-chromatography test strip can be inserted in the fixing table as well as positioned therein.

According to a sixty-eighth aspect of the present invention, in accordance with the chromatography quantitative measuring apparatus of the sixty-seventh aspect, the notch is provided asymmetrically with respect to the center line of the immuno-chromatography test strip in the longer-side direction.

Therefore, it is possible to prevent the immuno-chromatography test strip from being inserted in the fixing table inside out.

According to a sixty-ninth aspect of the present invention, in accordance with the chromatography quantitative measuring apparatus of the sixty-fifth aspect, the carrier is provided with a groove at its end on the side of insertion of the immuno-chromatography test strip into the fixing table, and the fixing table is provided with a projection which can be inserted in the groove.

Therefore, the immuno-chromatography test strip can be inserted in the fixing table as well as positioned therein, and further fixed in the fixing table.

According to a seventieth aspect of the present invention, the chromatography quantitative measuring apparatus of the sixty-ninth aspect, includes a means for detecting whether the projection is inserted in the groove.

Therefore, it is possible to recognize that the immuno-chromatography test strip is correctly disposed in the fixing table.

According to a seventy-first aspect of the present invention, in accordance with the chromatography quantitative measuring apparatus of the sixty-fifth aspect, the immuno-chromatography test strip is shaped to have stages by narrowing the width on the side of insertion into the fixing table. Therefore, the immuno-chromatography test strip can be inserted in the fixing table as well as positioned therein.

According to a seventy-second aspect of the present invention, in accordance with the chromatography quantitative measuring apparatus of the sixty-fifth aspect, the fixing table is provided with an elastic member for pressing the immuno-chromatography test strip.

Therefore, a part of the immuno-chromatography test strip where a beam is applied can be smoothed.

According to a seventy-third aspect of the present invention, in accordance with the chromatography quantitative measuring apparatus of the seventy-second aspect, the elastic member is integrated with the fixing table.

Therefore, it is possible to prevent a loss of the elastic member.

According to a seventy-fourth aspect of the present invention, in accordance with the chromatography quantitative measuring apparatus of the seventy-second aspect, the elastic member has its end inclined.

Therefore, the immuno-chromatography test strip can be smoothly inserted in the fixing table.

According to a seventy-fifth aspect of the present invention, the chromatography quantitative measuring apparatus of the seventy-second aspect, includes a mechanism for releasing the press by the elastic member.

Therefore, the immuno-chromatography test strip can be easily removed from the fixing table.

According to a seventy-sixth aspect of the present invention, the chromatography quantitative measuring apparatus of the fortieth aspect, includes an elastic member for pressing the immuno-chromatography test strip.

Therefore, the immuno-chromatography test strip can be easily attached to the fixing table, and a part where a beam is applied can be smoothed.

According to a seventy-seventh aspect of the present invention, in accordance with the chromatography quantitative measuring apparatus of the seventy-second or seventy-sixth aspect, the elastic member is detachable.

Therefore, it is possible to promptly cope with a case where the elastic member is defective.

According to a seventy-eighth aspect of the present invention, in accordance with the chromatography quantitative measuring apparatus of the fortieth aspect, an operator can hold the carrier to detach the immuno-chromatography test strip from the fixing table.

Therefore, an operator is not contaminated with a sample when detaching the immuno-chromatography test strip.

According to a seventy-ninth aspect of the present invention, in accordance with the chromatography quantitative measuring apparatus of the seventy-eighth aspect, the carrier is bent to create a space between the fixing table and the end of the carrier.

Therefore, the immuno-chromatography test strip can be detached easily.

According to an eightieth aspect of the present invention, in accordance with the chromatography quantitative measuring apparatus of the seventy-ninth aspect, the carrier is provided with a groove to be bent therealong.

Therefore, the carrier is easily bent, so that the immuno-chromatography test strip can be detached simply.

According to an eighty-first aspect of the present invention, in accordance with the chromatography quantitative measuring apparatus of the seventy-eighth aspect, the carrier protrudes above the fixing table.

Therefore, the carrier is easy for an operator to hold when detaching the immuno-chromatography test strip, resulting in enhancement in operationality.

According to an eighty-second aspect of the present invention, in accordance with the chromatography quantitative measuring apparatus of the seventy-eighth aspect, a part of the carrier is provided with a slip stopper.

Therefore, the carrier is easy for an operator to hold when detaching the immuno-chromatography test strip, resulting in enhancement in operationality.

According to an eighty-third aspect of the present invention, in accordance with the chromatography quantitative measuring apparatus of the fortieth aspect, the fixing table is provided with a groove for receiving the inspection target solution.

Therefore, a sample which erroneously escapes during the application of sample to the immuno-chromatography test strip is prevented from adhering to the measuring apparatus.

According to an eighty-fourth aspect of the present invention, in accordance with the chromatography quantitative measuring apparatus of the eighty-third aspect, the groove is given a slope, so that the inspection target solution can be supplied to the development layer from the direction of the cross section of the immuno-chromatography test strip.

Therefore, the fixing table is applicable to other types of test strips.

According to an eighty-fifth aspect of the present invention, in accordance with the chromatography quantitative measuring apparatus of the fortieth aspect, the fixing table is subjected to water repellent finishing.

Therefore, a sample which erroneously escapes during the application of sample to the immuno-chromatography test strip can be easily wiped.

According to an eighty-sixth aspect of the present invention, in accordance with the chromatography quantitative measuring apparatus of the fortieth aspect, the fixing table is attached with an absorbent material.

Therefore, a sample which erroneously escapes during the application of sample to the immuno-chromatography test strip is absorbed by the absorbent material, so that the sample is prevented from adhering to the measuring apparatus.

According to an eighty-seventh aspect of the present invention, in accordance with the chromatography quantitative measuring apparatus of the fortieth aspect, the fixing table has a through hole in which a removal bar can be inserted, and the bar is inserted in the through hole to press the immuno-chromatography test strip, thereby removing the immuno-chromatography test strip from the fixing table.

Therefore, an operator is not contaminated with a sample when detaching the immuno-chromatography test strip.

According to an eighty-eighth aspect of the present invention, in accordance with the chromatography quantitative measuring apparatus of the eighty-seventh aspect, the removal bar is integrated with the fixing table.

Therefore, it is possible to prevent a loss of the bar.

DETAILED DESCRIPTION OF THE INVENTION

Hereinafter, embodiments according to the present invention will be described with reference to the drawings. The embodiments described here are given only as examples and the present invention is not restricted to these embodiments.

First Embodiment

Hereinafter, a chromatography quantitative measuring apparatus that corresponds to the invention defined in the above-described first through sixth aspects of the present invention will be described as a first embodiment with reference to FIGS. 1(a) and 1(b).

Figure 25:
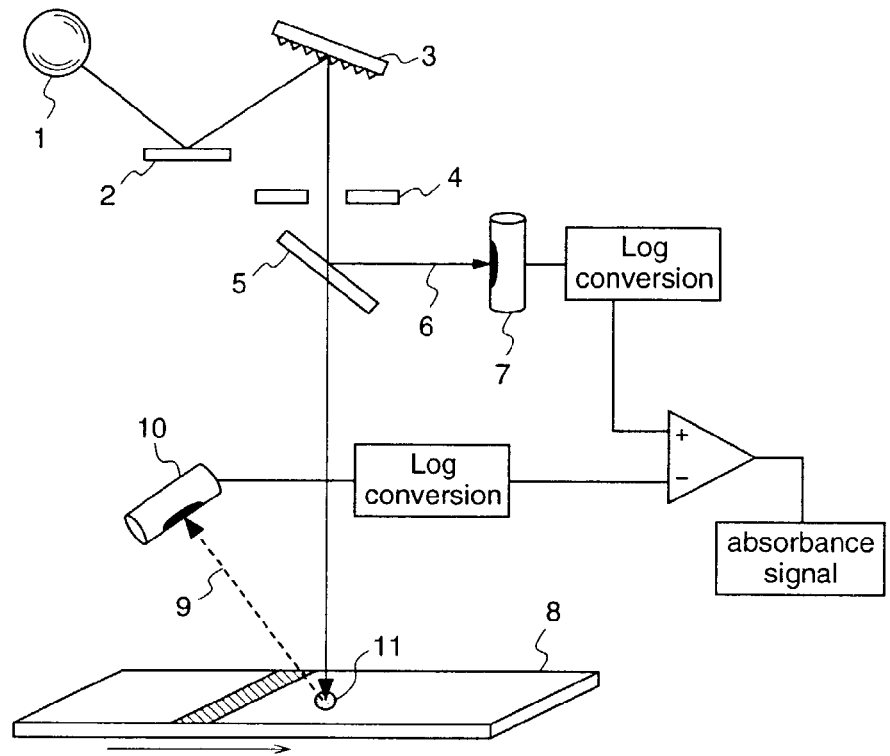
FIGS. 25(a)-25(c) are diagrams showing an example of a conventional chromatography quantitative measuring apparatus.
Figure 25:
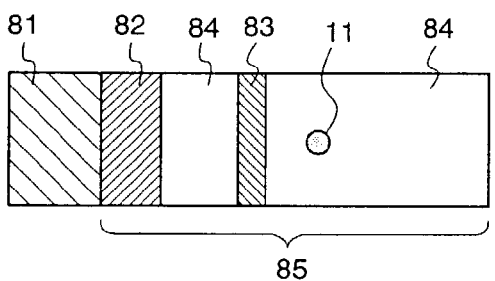
Figure 25:
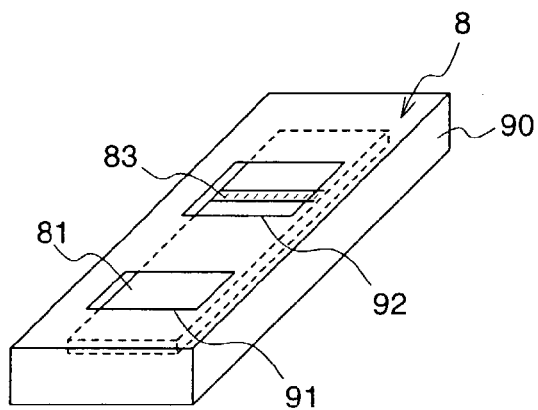

FIG. 1(a) is a diagram schematically illustrating the configuration of a reflective spectrophotometer as the chromatography quantitative measuring apparatus according to the first embodiment. FIG. 1(b) is a diagram illustrating the constitution of a chromatography test strip. In FIGS. 1(a) and 1(b), the same or corresponding constituent elements as those shown in FIGS. 25(a)-25(c) are denoted by the same reference numerals, and descriptions thereof will be omitted.

Figure 1:
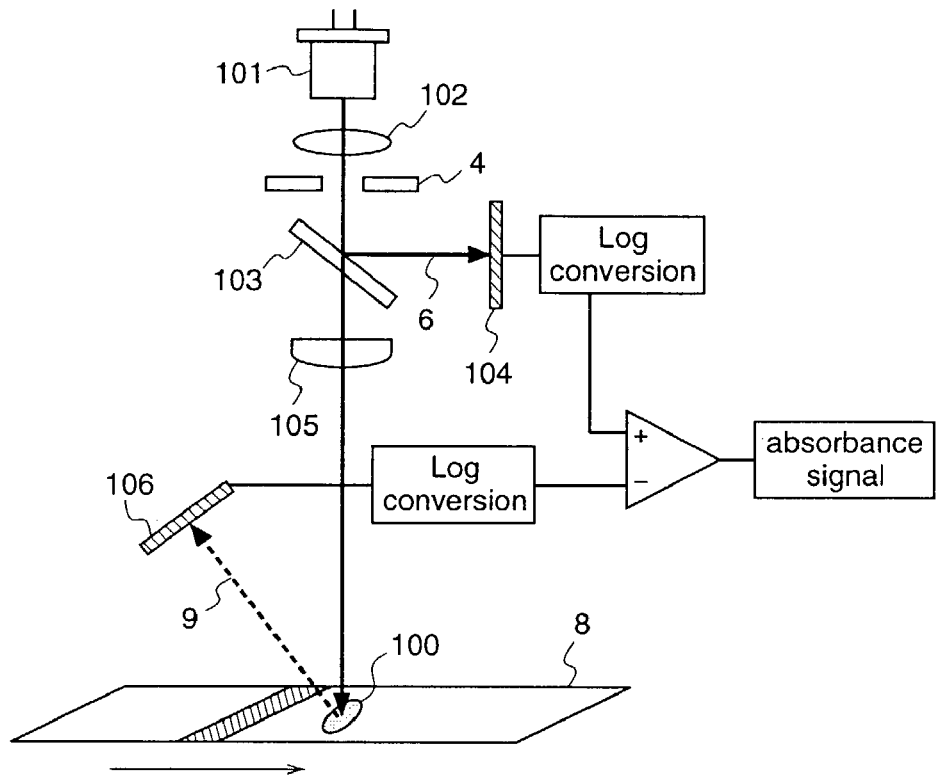
FIGS. 1(a) and 1(b) are diagrams illustrating the configuration of a chromatography quantitative measuring apparatus according to a first embodiment.
Figure 1:
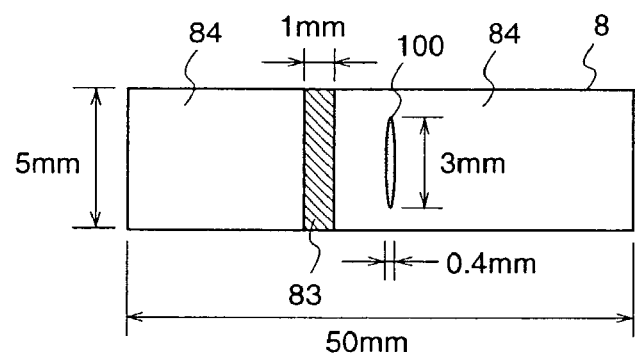

In FIG. 1, reference numeral 101 denotes a semiconductor laser as a light source, reference numeral 102 denotes a collimator lens which converts a beam emitted form the semiconductor laser 101 into a collimated beam, reference numeral 103 denotes a polarization beam splitter which polarizes the beam that has passed through the aperture 4, reference numeral 104 denotes a photodiode A which monitors the reference beam 6, and reference numeral 105 denotes a cylindrical lens which leads the beam that has passed through the polarization beam splitter 103 to the immuno-chromatography test strip 8. Reference numeral 106 denotes a photodiode B which receives the scattering light 9 from the immuno-chromatography test strip 8.

An operation of the so-configured chromatography quantitative measuring apparatus will be described.

When an inspection target solution is applied to the application part 81 and the sample is developed, a beam is applied to the chromatography test strip 8 from the semiconductor laser 101 in order to measure the concentration of an analysis target included in the inspection target solution. The beam emitted from the semiconductor laser 101 is converted into a collimated beam via the collimator lens 102. The wavelength of the semiconductor laser 101 is 635 nm. The wavelength is so decided for the reason that by this wavelength, there can be obtained a sufficient difference between absorbance of a gold colloid as a marker regent and absorbance of blood (erythrocyte) as a sample, as well as sufficient absorbance sensitivity of the gold colloid, and this wavelength is used for an optical disk or the like.

The collimated beam obtained by the collimator lens 102 is input to the polarization beam splitter 103 through the aperture 4 (3 mm). This polarization beam splitter 103 is used in order to take advantage of light effectively by utilizing the polarization characteristic of a laser. The beam reflected (separated) at the polarization beam splitter 103 is received by the photodiode A 104 as the reference beam 6. On the other hand, the beam transmitted through the polarization beam splitter 103 is input to the cylindrical lens 105. By the cylindrical lens 105, the beam is focused only in the direction orthogonal with respect to the width of the immuno-chromatography test strip 8 (the direction of a long side). As shown in FIG. 1(b), the immuno-chromatography test strip 8 described with respect to the first embodiment is approximately 50 mm long by 5 mm wide, and the detection part 83 thereof is approximately 1 mm long. Accordingly, the beam applied in the first embodiment is an elliptical beam 100 which has a major axis of 3 mm and a minor axis of 0.4 mm, in consideration of an error in attachment of the immuno-chromatography test strip 8, the accuracy of scanning, and the like. When the elliptical beam 100 is constituted by the cylindrical lens 105, the efficiency in light utilization will be five times as high as that when the elliptical beam 100 is constituted by the aperture 4.

Then, the scattering light 9 from the immuno-chromatography test strip 8 is received by the photodiode B 106. The photodiode B 106 is arranged 30 mm apart from the sample with an inclination of 45° with respect to the axis of the beam applied to the immuno-chromatography test strip 8. The area of the photodiode B 106 for receiving light is 10×10 mm, where the scattering light 9 with power approximately $\frac{1}{1000}$ as high as the emission power of the semiconductor laser 101 is received.

Outputs from the photodiodes 104 and 106, which have received the reference beam 6 and the scattering light 9 in this way, are respectively subjected to Log transformation, and a value obtained by doing subtraction with these Log transformed values is output as an absorbance signal.

By the above-described configuration, light is effectively utilized by using the laser, whereby a measurement is fairly possible with the photodiodes even without any use of a photomultiplier tube, resulting in a reduction in the cost of the apparatus. A previously-obtained calibration curve indicates a relationship between the difference between the absorbance signal of the base part 84 at the immuno-chromatography test strip 8 and the absorbance signal at the detection part 83, and the concentration of a sample to be measured. By detecting the difference between the absorbance signal at the base part 84 and that at the detection part 83 where an actual sample is applied, the concentration of the sample is obtained through the calibration curve in consideration of a known difference between the absorbance signal at the base part 84 and that at the detection part 83. In the above-described configuration, the immuno-chromatography test strip 8 is scanned in the longitudinal direction, thereby measuring the difference between the absorbance signal at the base part 84 and that at the detection part 83 with a single beam. Further, when the beam is also scanned by moving the whole optical system, the difference between the absorbance signal at the base part 84 and that at the detection part 83 can be similarly obtained with a single beam.

Further, the influence of non-uniform coloration in the direction of the width of the immuno-chromatography test strip 8 can be reduced by the elliptical beam. However, attention should be paid when the major axis of the elliptical beam is 5 mm or more, because the elliptical beam 100 might easily protrude beyond the immuno-chromatography test strip 8 due to scanning thereof or the like, which results in an error factor. Further, attention should also be paid with respect to the fact that sensitivity of the absorbance is low when the minor axis is 1 mm or more, and influence of non-uniform coloration is increased when the beam is totally focused, which results in an error factor.

Figure 2:
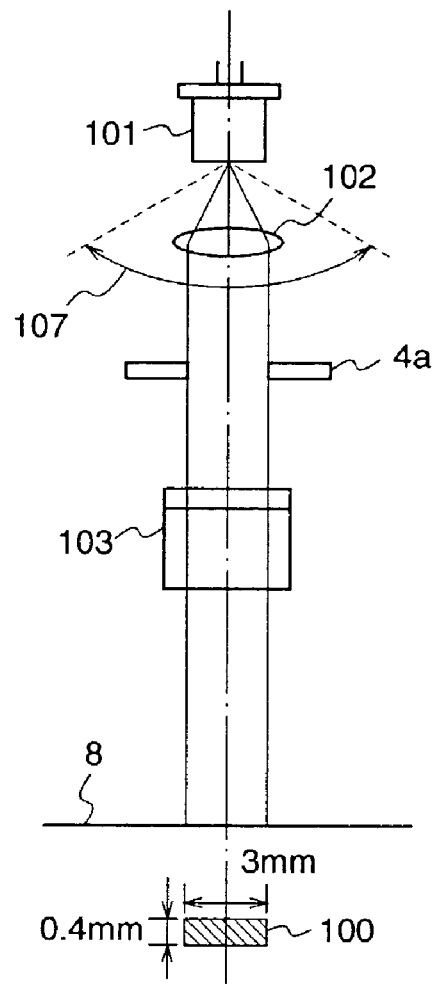
FIGS. 2(a) and 2(b) are cross sectional views of a chromatography quantitative measuring apparatus according to a second embodiment from the viewpoint of the direction in which a sample is developed, and from the viewpoint of the direction perpendicular to the direction in which the sample is developed, respectively.
Figure 2:
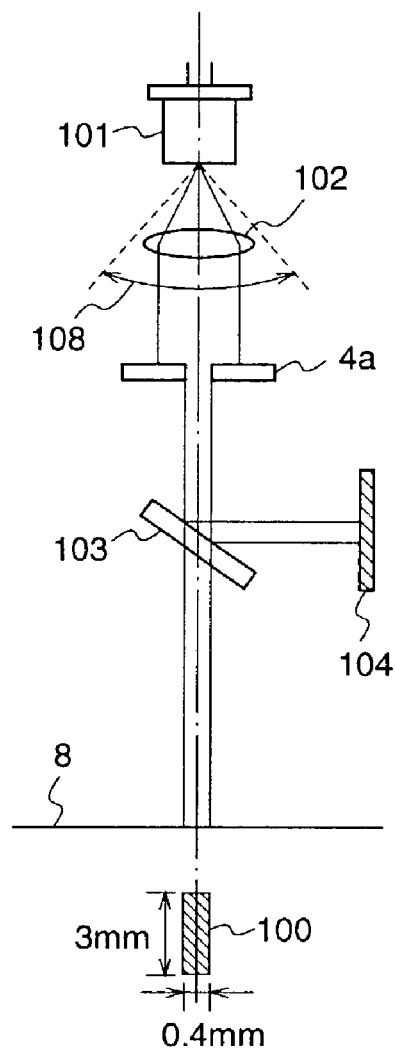

While the beam is formed into an elliptical shape by employing the cylindrical lens 105 in FIG. 1(a), the beam may be formed into a rectangular shape by employing a rectangular aperture 4a as shown in FIG. 2, instead of the aperture 4 in FIG. 1(a), and eliminating the cylindrical lens.

As described above, according to the chromatography quantitative measuring apparatus of the first embodiment, the semiconductor laser 101 is employed as a light source, the beam emitted therefrom is formed into an elliptical shape by an optical means such as the cylindrical lens 105, or into a rectangular shape by means of the aperture 4a, and the elliptically or rectangularly shaped beam is applied to the immuno-chromatography test strip 8 where a sample is applied. Therefore, a part as the light source can be downsized and the cost thereof is reduced. Further, by employing the beam in elliptical shape or the like, the influence of non-uniform coloration in the direction of the width of the immuno-chromatography test strip 8 can be reduced, thereby enhancing the accuracy of quantitative analysis.

Further, the difference between the absorbance signal at the base part 84 of the immuno-chromatography test strip 8 and the absorbance signal at the detection part 83 can be obtained by scanning the beam over the immuno-chromatography test strip 8, thereby performing an effective measurement.

Second Embodiment

Figure 3:
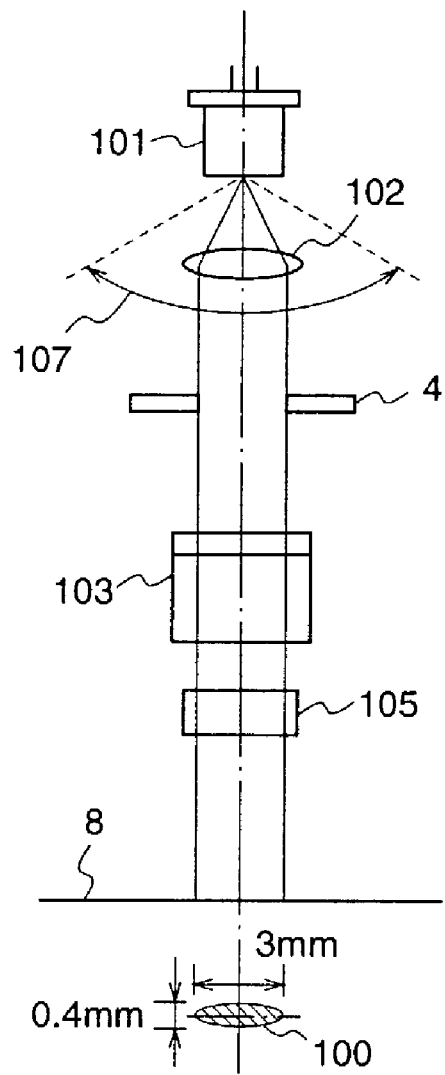
FIGS. 3(a) and 3(b) are cross sectional views of another chromatography quantitative measuring apparatus according to the second embodiment from the viewpoint of the direction in which the sample is developed, and from the viewpoint of the direction perpendicular to the direction in which the sample is developed, respectively.
Figure 3:
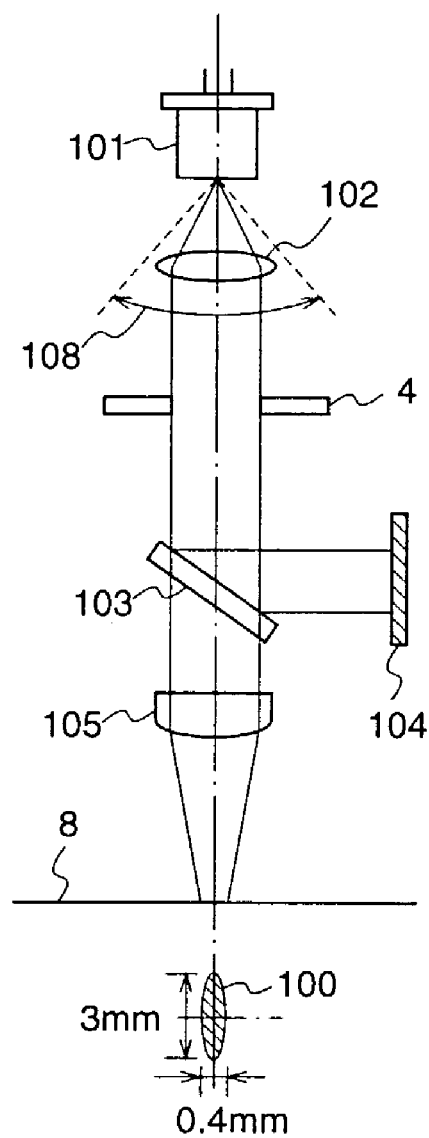

Next, a chromatography quantitative measuring apparatus that corresponds to the invention defined in the above-described seventh and eighth aspects of the present invention will be described as a second embodiment with reference to FIGS. 2 and 3.

FIGS. 2(a) and 2(b) are cross sectional views of an optical system, a reflective spectrophotometer, as the chromatography quantitative measuring apparatus according to the second embodiment, from the viewpoint of the direction in which a sample is developed (FIG. 2(a)), and from the viewpoint of the direction perpendicular to the direction in which the sample is developed (FIG. 2(b)).

In FIGS. 2(a) and 2(b), a beam emitted from the semiconductor laser 101 is converted into a collimated beam via the collimator lens 102. The collimated beam is input to the polarization beam splitter 103 through the aperture 4a (3×0.4 mm) Then, the beam reflected at the polarization beam splitter 103 is received by the photodiode A 104 as the reference beam 6. On the other hand, the beam transmitted through the polarization beam splitter 103 is applied to the immuno-chromatography test strip 8. As described above, the immuno-chromatography test strip 8 according to the second embodiment is also approximately 50 mm long by 5 mm wide, and the detection part 83 thereof is approximately 1 mm long. Accordingly, the beam applied in the second embodiment is a rectangular beam 100 which has a longer side of 3 mm and a shorter side of 0.4 mm, in consideration of an error in attachment of the immuno-chromatography test strip 8, the accuracy of scanning, and the like. In the configuration in FIGS. 2(a) and 2(b), at this time, when the direction 107 in which the beam divergence angle of the semiconductor laser 101 becomes larger is made to correspond to direction of a longer side of the rectangular beam, the direction 108 in which the beam divergence angle of the semiconductor laser 101 becomes smaller corresponds to the direction of a shorter side of the rectangular beam, resulting in disposition with the highest light utilization efficiency. Further, since distribution of optical power in the longer-side direction is smoothed, non-uniform coloration in the direction of the width of the immuno-chromatography test strip 8 is further reduced.

Further, FIGS. 3(a) and 3(b) are cross sectional views of another optical system as a reflective spectrophotometer according to the second embodiment, from the viewpoint of the direction in which a sample is developed (FIG. 3(a)), and from the viewpoint of the direction perpendicular to the direction in which the sample is developed (FIG. 3(b)).

In FIGS. 3(a) and 3(b), a beam emitted from the semiconductor laser 101 is converted into a collimated beam via the collimator lens 102. The collimated beam is input to the polarization beam splitter 103 through the aperture 4 (Ø3 mm). Then, the beam reflected at the polarization beam splitter 103 is received by the photodiode A 104 as the reference beam 6. On the other hand, the beam transmitted through the polarization beam splitter 103 is input to the cylindrical lens 105. By the cylindrical lens 105, the beam is focused only in the direction orthogonal with respect to the width (the direction of a long side) of the immuno-chromatography test strip 8. As described above, the beam to be applied is the elliptical beam 100 which has a major axis of 3 mm and a minor axis of 0.4 mm, in consideration of an error in attachment of the immuno-chromatography test strip 8, the accuracy of scanning, and the like. In the configuration in FIGS. 3(a) and 3(b), at this time, when the direction 107 in which the beam divergence angle of the semiconductor laser 101 becomes larger is made to correspond to the direction of the major axis of the elliptical beam, the direction 108 in which the beam divergence angle of the semiconductor laser 101 becomes smaller corresponds to the direction of the minor axis of the elliptical beam. Therefore, as compared with the configuration shown with respect to the first embodiment in FIG. 1(a), which does not adopt the above-described construction of making the direction 107 in which the beam divergence angle of the semiconductor laser 101 becomes larger correspond to the direction of the major axis of the elliptical beam, while there is no difference in the light utilization efficiency, distribution of optical power in the direction of the major axis is smoothed, and thus non-uniform coloration in the direction of the width of the immuno-chromatography test strip 8 is further reduced.

As described above, according to the chromatography quantitative measuring apparatus of the second embodiment, the direction 107 in which the beam divergence angle of the laser beam emitted from the semiconductor laser 101 becomes larger is made to correspond to the direction of a longer side of the beam which is shaped rectangularly by employing the aperture 4a, or to the direction of the major axis of the beam which is shaped elliptically by employing the cylindrical lens 105. Further, the beam is applied so that the direction of a long side (the direction of a longer side, or the direction of the major axis) of the beam is orthogonal with respect to the direction of a long side of the immuno-chromatography test strip 8. Thereby, distribution of optical power of the beam in the direction of the major axis is smoothed, and thus, non-uniform coloration in the direction of the width of the immuno-chromatography test strip 8 is further reduced.

Third Embodiment

Hereinafter, a chromatography quantitative measuring apparatus that corresponds to the invention defined in the above-described ninth and tenth aspects of the present invention will be described as a third embodiment with reference to FIG. 4.

Figure 4:
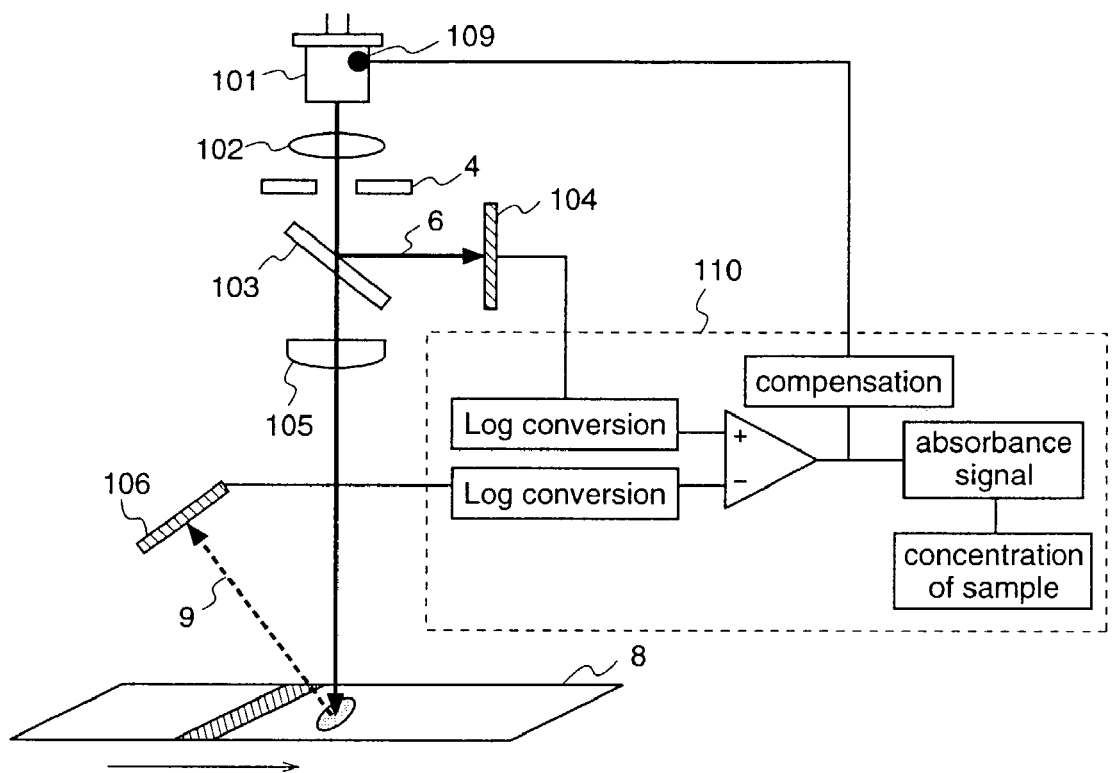
FIG. 4 is a diagram illustrating the configuration of a chromatography quantitative measuring apparatus according to a third embodiment.

FIG. 4 is a diagram schematically illustrating the configuration of a reflective spectrophotometer as the chromatography quantitative measuring apparatus according to the third embodiment. In FIG. 4, the same or corresponding constituent elements as those shown in FIGS. 1(a) and 1(b) are denoted by the same reference numerals, and descriptions thereof will be omitted.

In FIG. 4, reference numeral 109 denotes a temperature sensor provided in the vicinity of the semiconductor laser 101, and reference numeral 110 denotes a calculator which calculates the concentration of a sample from an absorbance signal that is compensated with reference to output from the temperature sensor 109. In the calculator 110 for performing compensation, Log transformation circuits for detecting optical signals and a circuit that constitutes a difference device for obtaining the converted concentration of the sample, or the like are integrally configured.

An operation of the so-configured chromatography quantitative measuring apparatus will be described.

When an inspection target solution is applied to the application part 81 and the sample is developed, a beam is applied to the chromatography test strip 8 from the semiconductor laser 101 in order to measure the concentration of an analysis target included in the inspection target solution. The beam emitted from the semiconductor laser 101 is converted into a collimated beam via the collimator lens 102. The wavelength of the semiconductor laser 101 is 635 nm. The collimated beam is input to the polarization beam splitter 103 through the aperture 4 (Ø3 mm). The beam reflected at the polarization beam splitter 103 is received by the photodiode A 104 as the reference beam 6. On the other hand, the beam transmitted through the polarization beam splitter 103 is input to the cylindrical lens 105, and is focused only in the direction orthogonal with respect to the width (the direction of a long side) of the immuno-chromatography test strip 8 by the cylindrical lens 105. Then, the scattering light 9 from the immuno-chromatography test strip 8 is received by the photodiode B 106. Outputs from the photodiodes 104 and 106, which have received the reference beam 6 and the scattering light 9, are respectively subjected to A/D conversion and input to the calculator 110.

Here, for example, in a case where a marker reagent is a gold colloid and a sample is blood (erythrocyte), when the wavelength of the beam from the semiconductor laser 101 is changed from 635 nm to 655 nm, the absorbance is reduced by approximately 30%. Further, according to temperature change, the wavelength is changed by approximately 0.2 nm/° C. in case of, for example, a commercially available semiconductor laser HL6333MG which is manufactured by Hitachi, Ltd. Thus, a large margin of error is generated unless there is compensation.

As described above, since an error in the absorbance is generated due to a variation of the wavelength of the beam, the initial wavelength of the semiconductor laser 101 is input to the calculator, and the amount of temperature change is detected by the temperature sensor 109 provided in the vicinity of the semiconductor laser 101 and input to the calculator. Then, in the calculator 110, outputs from the photodiodes 104 and 106 are subjected to Log transformation, and subtraction is performed with these Log transformed values, thereby obtaining an absorbance signal. At this time, the present wavelength is calculated from the initial wavelength of the semiconductor laser 101 and the amount of temperature change, and the absorbance signal is compensated from this present wavelength. Finally, the concentration of a sample is obtained from this compensated absorbance signal.

As described above, the chromatography quantitative measuring apparatus according to the third embodiment includes the temperature sensor 109 provided in the vicinity of the semiconductor laser 101, and the calculator 110 which calculates the concentration of a sample by compensating a value of difference between outputs from the photodiodes 104 and 106 on the basis of the output from the temperature sensor 109. Therefore, an influence due to hardware configuration and usage environment is reduced, resulting in a quantitative measurement with fewer measurement errors.

Further, the Log transformation circuits for detecting optical signals, and the circuits which constitute the difference device for obtaining the converted concentration of the sample, or the like are integrally configured, thereby reducing the size of the apparatus.

While in the third embodiment a description has been given of the case where the temperature sensor 109 and the calculator 110 are provided in the chromatography quantitative measuring apparatus shown in FIG. 1(a), the chromatography quantitative measuring apparatus shown in FIGS. 2(a) and 2(b) may be also provided with the temperature sensor 109 and the calculator 110, so that the present wavelength is calculated from the initial wavelength of the semiconductor laser 101 and the amount of temperature change, and an absorbance signal is compensated from this present wavelength.

Fourth Embodiment

Next, a chromatography quantitative measuring apparatus that corresponds to the invention defined in the above-described eleventh to thirteenth aspects of the present invention will be described as a fourth embodiment with reference to FIG. 5.

Figure 5:
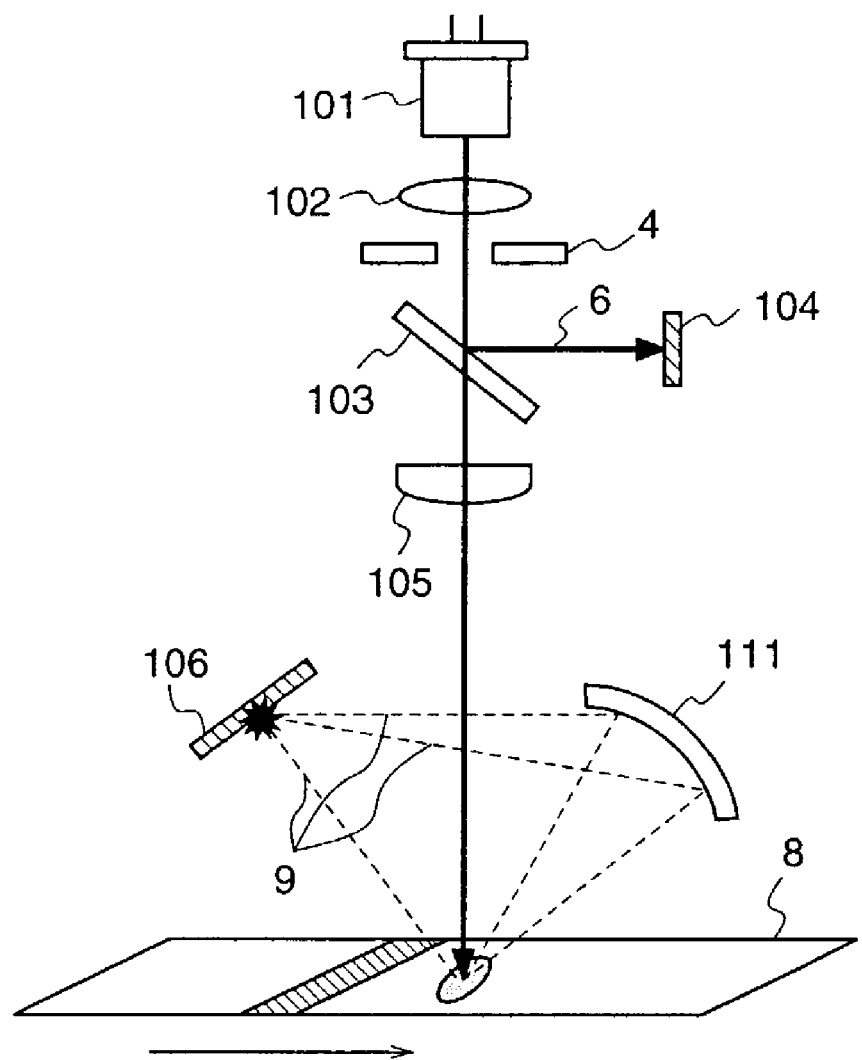
FIG. 5 is a diagram illustrating the configuration of a chromatography quantitative measuring apparatus according to a fourth embodiment.

FIG. 5 is a diagram schematically illustrating the configuration of a reflective spectrophotometer as the chromatography quantitative measuring apparatus according to the fourth embodiment. In FIG. 5, the same or corresponding constituent elements as those shown in FIGS. 25(a)-25(c) are denoted by the same reference numerals, and descriptions thereof will be omitted.

In FIG. 5, reference numeral 111 denotes a concave mirror which condenses the scattering light 9 from the immuno-chromatography test strip 8.

An operation of the so-configured chromatography quantitative measuring apparatus will be described.

When an inspection target solution is applied to the application part 81 and the sample is developed, a beam is applied to the chromatography test strip 8 from the semiconductor laser 101 in order to measure the concentration of an analysis target included in the inspection target solution. The beam emitted from the semiconductor laser 101 is converted into a collimated beam via the collimator lens 102. The collimated beam is input to the polarization beam splitter 103 through the aperture 4 (Ø3 mm). The beam reflected at the polarization beam splitter 103 is received by the photodiode A 104 as the reference beam 6. On the other hand, the beam transmitted through the polarization beam splitter 103 is input to the cylindrical lens 105, and is focused only in the direction orthogonal with respect to the width (the direction of a long side) of the immuno-chromatography test strip 8 by the cylindrical lens 105. Then, the scattering light 9 from the immuno-chromatography test strip 8 is received by the photodiode B 106. At this time, the concave mirror 111 condenses a scattering light from the immuno-chromatography test strip 8 which goes in the opposite direction of a scattering light that goes toward the photodiode B 106, with the laser beam input from the semiconductor laser 101 to the immuno-chromatography test strip 8 as an axis of symmetry, on the photodiode B 106.

The photodiode B 106 is arranged 30 mm apart from the sample with an inclination of 45° with respect to the axis of the beam applied to the immuno-chromatography test strip 8. The area of the photodiode B 106 for receiving light is 10×10 mm, where the scattering light 9 with power approximately 1/1000 as high as the emission power of the semiconductor laser 101 is received. Outputs from the photodiodes A 104 and B 106, which have received the reference beam 6 and the scattering light 9, are respectively subjected to Log transformation, and the result of subtraction with these Log transformed values is output as an absorbance signal, as described in FIG. 1. A previously-obtained calibration curve indicates a relationship between the difference between the absorbance signal at the base part 84 of the immuno-chromatography test strip 8 and the absorbance signal at the detection part 83, and the concentration of sample to be measured. By detecting the difference between the absorbance signal at the base part 84 and that at the detection part 83 where an actual sample is applied, the concentration of the sample is obtained through the calibration curve in consideration of a known difference between the absorbance signal at the base part 84 and that at the detection part 83. At this time, the reference beam 6 has a beam diameter of Ø3 mm, and thus, the area of the photodiode A 104 for receiving light may be approximately 5×5 mm, resulting in a photodiode that is lower in price than the photodiode B 106. Further, by using the concave mirror 111, the scattering light 9 can be condensed more effectively, resulting in a measurement of the absorbance with a higher S/N ratio.

As described above, the chromatography quantitative measuring apparatus according to the fourth embodiment is provided with the concave mirror 111, so that, among the scattering light 9 from the immuno-chromatography test strip 8, a scattering light which goes in the symmetrical direction with respect to the direction of the photodiode B 106, with the optical axis of the semiconductor laser as an axis of symmetry, is effectively condensed on the photodiode B 106. Therefore, a measurement of the absorbance with a higher S/N ratio can be performed.

While in the fourth embodiment a description has been given by taking, as an example, the case where the area of the photodiode A 104 for receiving light is reduced and the concave mirror 111 is provided in the chromatography quantitative measuring apparatus shown in FIG. 1, the chromatography quantitative measuring apparatus shown in FIG. 2 is similarly applicable.

Fifth Embodiment

Next, a chromatography quantitative measuring apparatus that corresponds to the invention defined in the above-described fourteenth aspect of the present invention will be described as a fifth embodiment with reference to FIG. 6.

Figure 6:
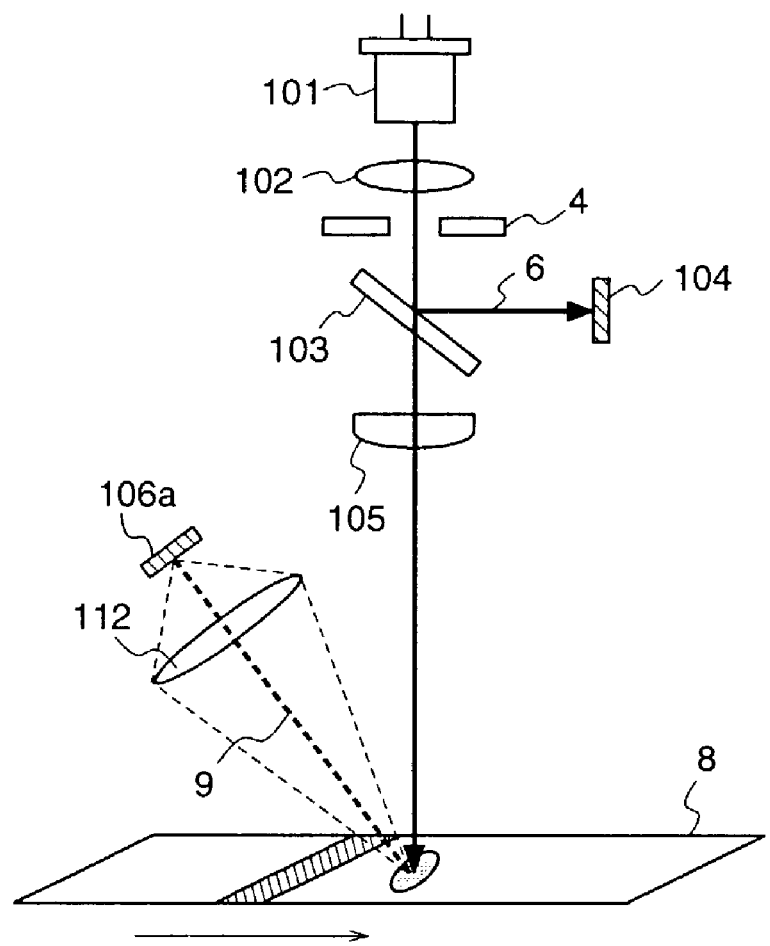
FIG. 6 is a diagram illustrating the configuration of a chromatography quantitative measuring apparatus according to a fifth embodiment.

FIG. 6 is a diagram schematically illustrating the configuration of a reflective spectrophotometer as the chromatography quantitative measuring apparatus according to the fifth embodiment. In FIG. 6, the same or corresponding constituent elements as those shown in FIGS. 25(a)-25(c) are denoted by the same reference numerals, and descriptions thereof will be omitted.

In FIG. 6, reference numeral 112 denotes a condensing lens for effectively condensing the scattering light 9 from the immuno-chromatography test strip 8 on a photodiode B 106a that is smaller than the above-described photodiode B 106.

An operation of the so-configured chromatography quantitative measuring apparatus will be described.

When an inspection target solution is applied to the application part 81 and the sample is developed, a beam is applied to the chromatography test strip 8 from the semiconductor laser 101 in order to measure the concentration of an analysis target included in the inspection target solution. The beam emitted from the semiconductor laser 101 is converted into a collimated beam via the collimator lens 102. The collimated beam is input to the polarization beam splitter 103 through the aperture 4 (Ø3 mm). The beam reflected at the polarization beam splitter 103 is received by the photodiode A 104 as the reference beam 6. On the other hand, the beam transmitted through the polarization beam splitter 103 is input to the cylindrical lens 105, and is focused only in the direction orthogonal with respect to the direction of a long side of the immuno-chromatography test strip 8 by the cylindrical lens 105. Then, the scattering light 9 from the immuno-chromatography test strip 8 is received by the photodiode B 106a. At this time, the condensing lens 112 is arranged in front of the photodiode B 106a, and the scattering light 9 is effectively condensed by this condensing lens 112.

Outputs from the photodiodes A 104 and B 106a, which have received the reference beam 6 and the scattering light 9, are respectively subjected to Log transformation, and the result of subtraction with these Log transformed values is output as an absorbance signal, as described in FIG. 1. A previously-obtained calibration curve indicates a relationship between the difference between the absorbance signal at the base part 84 of the immuno-chromatography test strip 8 and the absorbance signal at the detection part 83, and the concentration of a sample to be measured. By detecting the difference between the absorbance signal at the base part 84 and that at the detection part 83 where an actual sample is applied, the concentration of the sample is obtained through the calibration curve in consideration of a known difference between the absorbance at the base part 84 and that at the detection part 83.

As described above, the chromatography quantitative measuring apparatus according to the fifth embodiment is provided with the condensing lens 112 which effectively condenses a scattering light that goes toward the photodiode B 106a, among the scattering light 9 from the immuno-chromatography test strip 8, on the photodiode B 106a. Therefore, the area of the photodiode B 106a for receiving light, that is, the size of the photodiode B 106a, can be reduced without decreasing the amount of light received by the photodiode B 106a, whereby a low cost photodiode can be adopted, resulting in a reduction in the cost and size of the apparatus.

Further, by reducing the areas of the photodiode A 104 and photodiode B 106a for receiving lights, a speed of response of the photodiodes can be improved, and thus, a speed of scanning of the immuno-chromatography test strip 8 is improved, thereby shortening a measurement time.

While in the fifth embodiment a description has been given by taking, as an example, the case where the condensing lens 112 is provided and the area of the photodiode B 106 is reduced in the chromatography quantitative measuring apparatus shown in FIG. 1, the chromatography quantitative measuring apparatuses shown in FIGS. 2(a)-2(b) and 3(a)-3(b) may be also provided with the condensing lens 112 between the photodiode B 106 for receiving a scattering light and the immuno-chromatography test strip 8, so that the scattering light 9 is received effectively.

Sixth Embodiment

Figure 7:
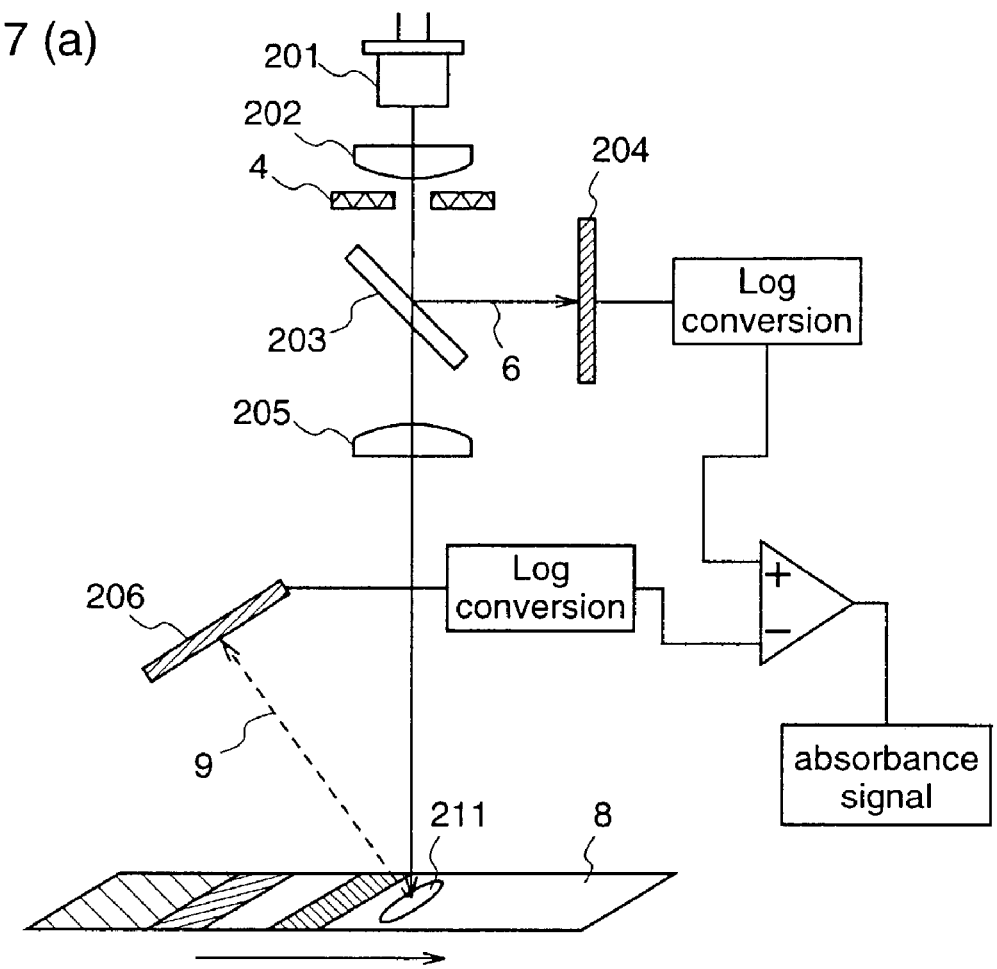
FIGS. 7(a) and 7(b) are diagrams schematically illustrating the configuration of a chromatography quantitative measuring apparatus according to a sixth embodiment.
Figure 7:
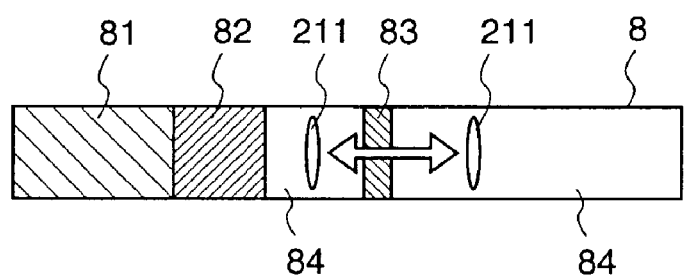

Hereinafter, a chromatography quantitative measuring apparatus that corresponds to the invention defined in the above-described fifteenth to nineteenth aspects of the present invention will be described as a sixth embodiment with reference to FIGS. 7 and 8.

FIGS. 7(a) and 7(b) are diagrams schematically illustrating the configuration of the chromatography quantitative measuring apparatus according to the sixth embodiment of the present invention. FIG. 7(a) is a diagram schematically illustrating the configuration of the measuring apparatus, and FIG. 7(b) is a diagram illustrating the constitution of a chromatography test strip.

In FIG. 7(a), a beam emitted from a semiconductor laser 201 is converted into a collimated beam by passing through a collimator lens 202. The collimated beam is input to a beam splitter 203 through the aperture 4. Here, a part of the optical beam reflected at the beam splitter 203 is received by a first photodiode 204 as the reference beam 6. On the other hand, the rest of the optical beam that is transmitted through the beam splitter 203 is condensed by a cylindrical lens 205 only in the direction of a longer side of the immuno-chromatography test strip 8, and is applied to the chromatography test strip 8 as an elliptical beam 211. Further, the scattering light 9 is generated from the surface of the chromatography test strip 8 and received by a second photodiode 206.

Next, outputs from the first photodiode 204 which has received the reference beam 6 and the second photodiode 206 which has received the scattering light 9 are respectively subjected to Log transformation, and a value obtained by subtracting a Log transformed value for the second photodiode 206 from a Log transformed value for the first photodiode 204 is output as an absorbance signal.

As shown in FIG. 7(b), the chromatography test strip 8 comprises the application part 81 where an inspection target solution is applied, the marker reagent hold part 82 which holds a marker reagent which can be eluted by development of the inspection target solution, a base part 84 where a specific binding reaction is caused between the marker reagent and an analysis target included in the inspection target solution, and a detection part 83 where a bounded material of the marker reagent and the analysis target is immobilized.

An operation of the so-configured chromatography quantitative measuring apparatus will be described with reference to FIGS. 7(a) and 7(b).

First, when an inspection target solution is applied to the application part 81, the inspection target solution is developed. At this time, when the inspection target solution reaches the marker reagent hold part 82, a marker reagent is eluted and specifically bonded to an analysis target included in the inspection target solution. Then, this bounded material is immobilized at the detection part 83, and a non-immobilized residual marker reagent flows downstream in the direction of the development, without being immobilized.

By detecting the difference between the absorbance signal at the detection part 83 of the chromatography test strip 8 and the absorbance signal at the base part 84, the concentration of the analysis target included in the inspection target solution can be converted through a known calibration curve.

Here, by scanning the chromatography test strip 8 in the longer-side direction, the difference between the absorbance signal at the base part 84 and that at the detection part 83 can be measured with a single beam. Further, since the optical beam is elliptical, the influence of non-uniform coloration according to positions in the direction of a shorter side of the chromatography test strip 8 is reduced.

Next, a description will be given of a measurement of the absorbance.

Figure 8:
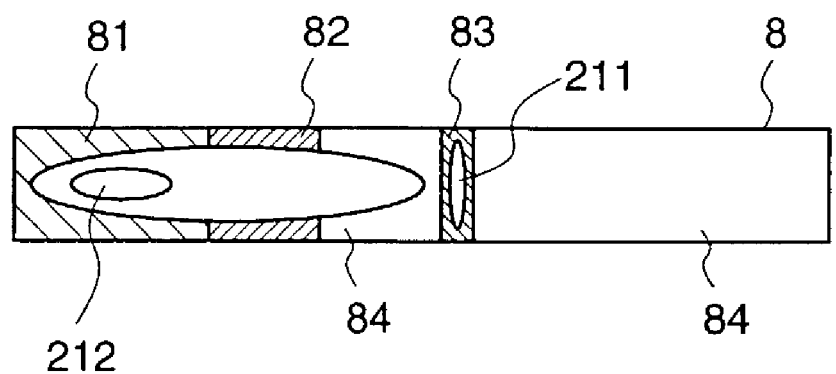
FIGS. 8(a) and 8(b) are diagrams showing a change in absorbance which accompanies development of an inspection target solution, according to the sixth embodiment.
Figure 8:
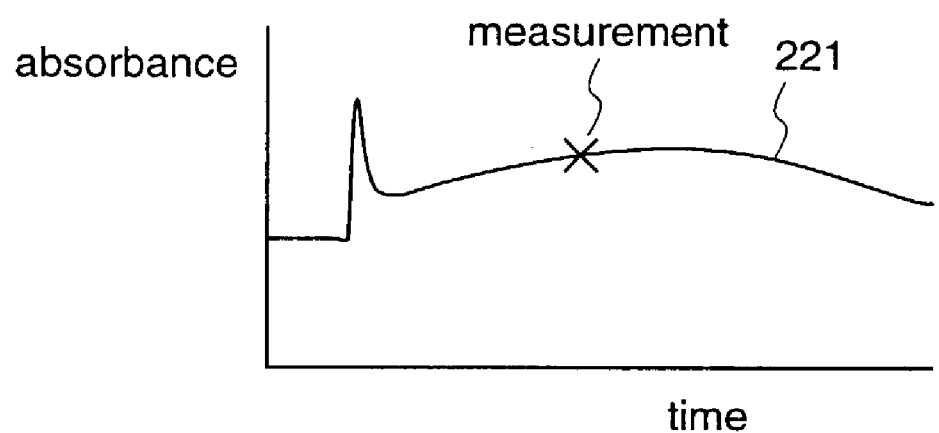

FIGS. 8(*a*) and 8(*b*) are diagrams illustrating the measurement of the absorbance on the chromatography test strip according to the sixth embodiment of the present invention. FIG. 8(*a*) illustrates a state where the inspection target solution is developed on the chromatography test strip 8 and a position where the optical beam is applied. FIG. 8(*b*) illustrates a change in absorbance signal with respect to a measurement time.

The chromatography test strip 8 is attached to the measuring apparatus, and an inspection target solution 212 is applied to the application part 81. With development of the inspection target solution 212, an analysis target included in the inspection target solution 212 is carried away, while being bounded to an eluted marker reagent, and a bounded material is immobilized at the detection part 83. When the absorbance is measured in a state where the optical beam 211 is continuously applied to the detection part 83, an absorbance signal 221 fluctuates sharply due to the passing of the marker reagent, then rises gradually, and falls gradually again as the inspection target solution is dried.

In order to reduce an error in the measurement of the absorbance, the optical beam 211 is kept being applied between the marker reagent hold part 82 and the downstream end of the base part 84, a change in absorbance due to the elution of the marker reagent is detected, and a measurement is automatically started after passage of prescribed period of time since the detection of the change in absorbance.

The above-mentioned prescribed period of time could affect a speed of development of the inspection target solution according to temperature and humidity around the measuring apparatus. Then, temperature and humidity are monitored from when the marker reagent is eluted with the development of the inspection target solution until when the concentration of the analysis target is measured, thereby compensating the prescribed period of time. Further, the optical beam is repeatedly lighted and extinguished alternately while the development of the inspection target solution is detected. Alternatively, a time to detect the development of the inspection target solution is predicted, and the optical beam is extinguished until shortly before the predicted arrival time. Alternatively, an output of the optical beam is set lower than that at measurement while the development of the inspection target solution is detected.

As described above, according to the chromatography quantitative measuring apparatus of the sixth embodiment, the inspection target solution is applied to the chromatography test strip 8, and the concentration of the analysis target included in the inspection target solution is measured after a prescribed period of time since the elution of the marker reagent, which accompanies the development of the inspection target solution, is detected. Therefore, an inspector does not need to manage time manually, and a used test strip where a marker reagent is already eluted can be discriminated because the measurement is performed after the elution of the marker reagent is detected.

Further, a surrounding temperature and humidity are monitored, so that time from when the elution of the marker reagent is detected until when the measurement is performed is compensated, thereby reducing the influence of a surrounding temperature and humidity on a variation in speed of development of the inspection target solution on the chromatography test strip.

Furthermore, the optical beam is repeatedly lighted and extinguished alternately while the development of the inspection target solution is detected. Alternatively, a time to detect the development of the inspection target solution is predicted, and the optical beam is extinguished until shortly before the predicted arrival time. Alternatively, laser output is set lower than that at measurement while the development of the inspection target solution on the chromatography test strip is detected. Alternatively, the above-described methods may be combined. Therefore, it is possible to prevent deterioration in the performance of the chromatography test strip, which accompanies a temperature rise at a part for applying a laser to the chromatography test strip.

While in the sixth embodiment a description has been given of the detection of the elution of the marker reagent, the same effect will be also achieved when the development of the inspection target solution itself is detected.

Seventh Embodiment

Next, a chromatography quantitative measuring apparatus that corresponds to the invention defined in the above-described twentieth to twenty-third aspects of the present invention will be described as a seventh embodiment with reference to FIGS. 9(*a*) and 9(*b*).

Figure 9:
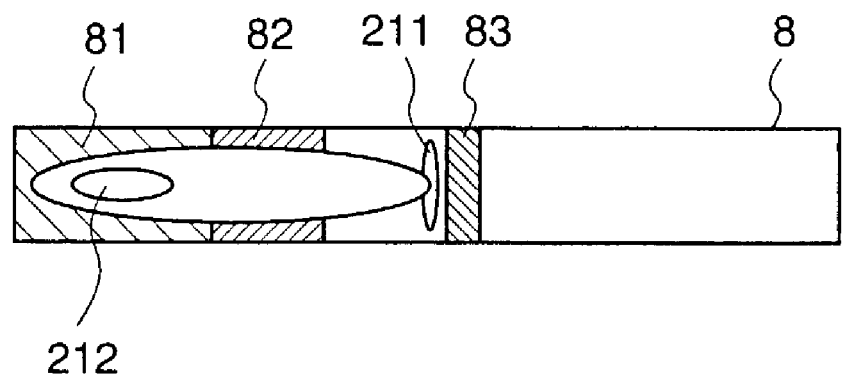
FIGS. 9(a) and 9(b) are diagrams showing a change in absorbance in a state where an optical beam is kept being applied according to a seventh embodiment.
Figure 9:
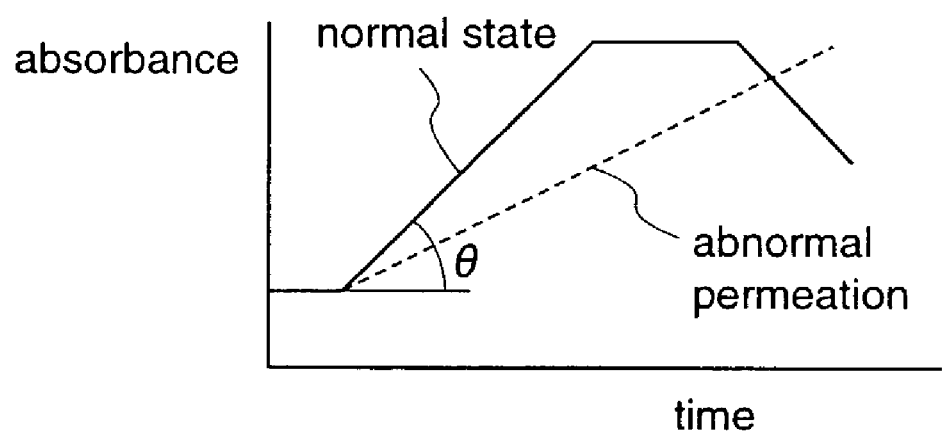

FIGS. 9(*a*) and 9(*b*) are diagrams illustrating a measurement of absorbance on a chromatography test strip according to the seventh embodiment of the present invention. FIG. 9(*a*) illustrates a state where the inspection target solution is developed on the chromatography test strip 8 and a position where an optical beam is applied. FIG. 9(*b*) is an enlarged view illustrating a sharp rise in a change in absorbance in a state where the optical beam is kept being applied according to the seventh embodiment of the present invention.

The optical beam 211 is kept being applied between the marker reagent hold part 82 and the detection part 83. The absorbance signal at this time increases monotonously with elution of the marker reagent.

By obtaining an inclination $\theta$ of the absorbance signal with respect to time variation, a speed of development of the inspection target solution 212 is calculated, and it is judged from the speed of development whether performance of the chromatography test strip is high or low. Alternatively, the optical beam is scanned so that a value of rise in absorbance, which is due to the elution of the marker reagent, is kept constant, the speed of development of the inspection target solution 212 is calculated from a speed of scanning, and it is judged from the speed of development whether the performance of the chromatography test strip 8 is high or low.

Further, a discrimination value of the speed of development is compensated from a result of measuring at least one of a surrounding temperature and humidity at the development of the inspection target solution on the chromatography test strip 8.

As described above, according to the chromatography quantitative measuring apparatus of the seventh embodiment, a speed of development of the inspection target solution after it is applied is detected, and it is judged from the speed of development whether performance of the chromatography test strip 8 is high or low. Therefore, it is possible to judge whether or not there is a defect such as abnormal clogging on the chromatography test strip 8.

Further, since the speed of development of the inspection target solution is calculated after the detection of a time variation of the value of a detection signal, which is generated by the elution of the marker reagent that accompanies the development of the inspection target solution, it is possible to judge whether or not there is a defect such as abnormal clogging on the chromatography test strip 8.

Furthermore, since the optical beam is scanned so that a value of the detection signal, which is generated by the elution of the marker reagent that accompanies the development of the inspection target solution, is kept constant, and the speed of development of the inspection target solution is calculated from a speed of scanning with the optical beam, it is possible to judge whether or not there is a defect such as abnormal clogging on the chromatography test strip 8.

Moreover, since a discrimination value of the speed of development is compensated from the result of measuring at least one of a surrounding temperature and humidity at the development of the inspection target solution, it is possible to prevent an erroneous judgement as to whether performance of the chromatography test strip is high or low, which is due to the influence of temperature or humidity.

Eighth Embodiment

Hereinafter, a chromatography quantitative measuring apparatus that corresponds to the invention defined in the above-described twenty-fourth to twenty-sixth aspects of the present invention will be described as an eighth embodiment with reference to FIGS. 10(*a*) and 10(*b*).

Figure 10:
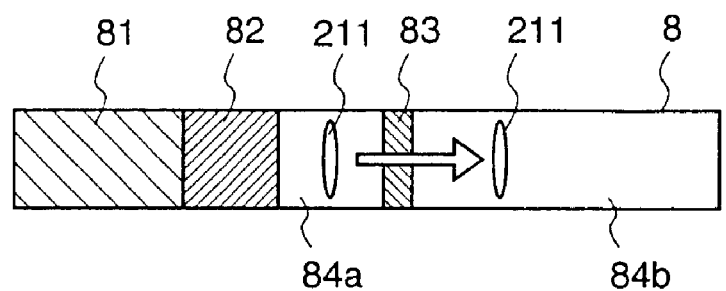
FIGS. 10(a) and 10(b) are diagrams showing results of measuring absorbances on a chromatography test strip when different inspection target solutions are employed, according to an eighth embodiment.
Figure 10:
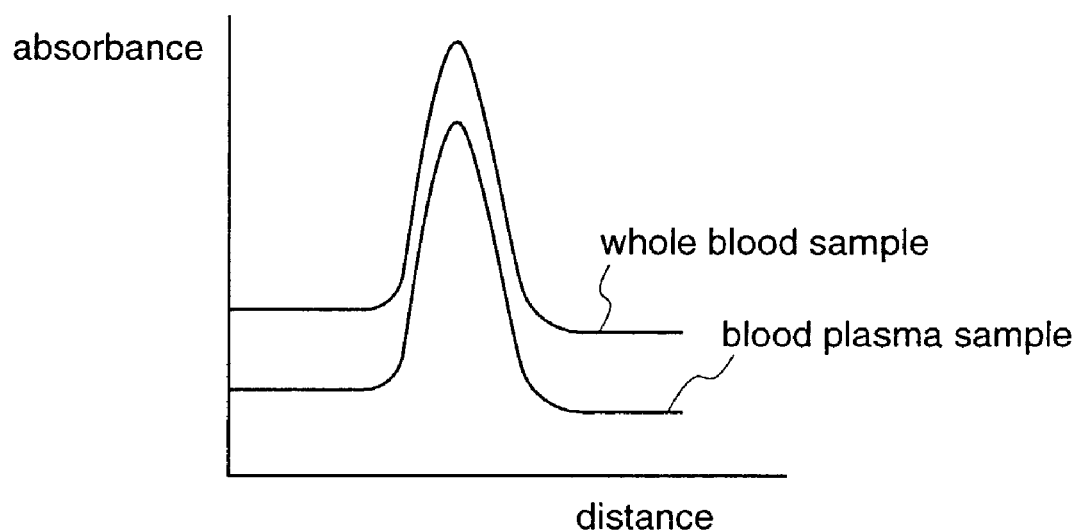

FIGS. 10(*a*) and 10(*b*) are diagrams showing results of measuring absorbances on the chromatography test strip 8 according to the eighth embodiment of the present invention, when different inspection target solutions are employed. FIG. 10(*a*) illustrates a state of scanning of an optical beam on the chromatography test strip 8. FIG. 10(*b*) shows changes of absorbance signals with respect to the position of the optical beam.

On the chromatography test strip 8, the optical beam 211 is scanned down to a downstream base part 84*b*, after passing through the detection part 83 from an upstream base part 84*a*. The absorbance signals at this time differ according to the kinds of inspection target solutions. For example, with respect to a whole blood sample and a blood plasma sample, the whole blood sample totally has a higher absorbance. Further, the absorbance at the base part 84 is constant regardless of the concentration of an analysis target included in the inspection target solution.

A signal detection position for discriminating a kind of inspection target solution is downstream of the detection part 83, and the absorbance at the base part 84 is detected and compared with a known absorbance that corresponds to the kind of each inspection target solution. Further, the kind of inspection target solution is discriminated from the absorbance at the base part 84, and a calibration curve corresponding to that kind is selected, thereby converting the concentration of the analysis target included in the inspection target solution.

As described above, according to the chromatography quantitative measuring apparatus of the eighth embodiment, a kind of inspection target solution is discriminated from the detection signal at the base part 84 on the chromatography test strip 8 where the inspection target solution is applied. Therefore, the kind of inspection target solution that is applied to the chromatography test strip 8 can be discriminated.

Further, since the base part 84 where the detection signal is measured is downstream of the detection part 83 in the direction of development, it is possible to prevent a discrimination of a kind of inspection target solution, which is due to influences of a marker reagent that is liable to remain at the base part 84*a* upstream of the detection part 83 as compared with the base part 84*b* downstream thereof.

Furthermore, since the kind of inspection target solution is discriminated from the detection signal at the base part 84, and a calibration curve corresponding to the inspection target solution can be selected previously, when plural kinds of inspection target solutions are measured, a user does not need to manually input a kind of inspection target solution to the apparatus, resulting in an automatic measurement.

Ninth Embodiment

Hereinafter, a chromatography quantitative measuring apparatus that corresponds to the invention defined in the above-described twenty-seventh and twenty-eighth aspects of the present invention will be described as a ninth embodiment with reference to FIGS. 11(*a*) and 11(*b*).

Figure 11:
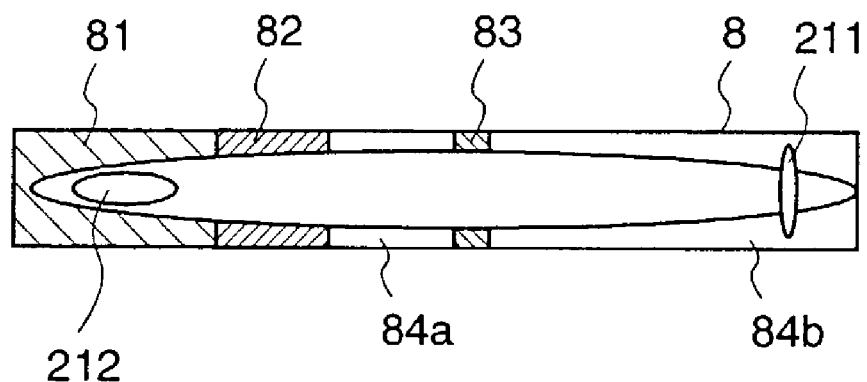
FIGS. 11(a) and 11(b) are diagrams illustrating the development of an inspection target solution on a chromatography test strip according to a ninth embodiment.
Figure 11:
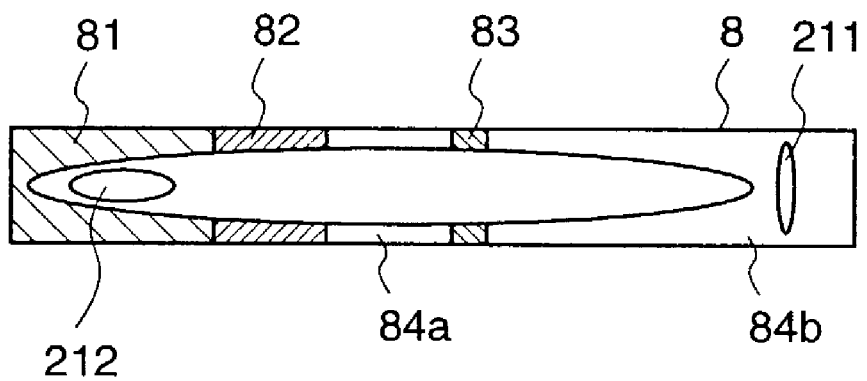

FIGS. 11(*a*) and 11(*b*) are diagrams illustrating streams of an inspection target solution on a chromatography test strip according to the ninth embodiment of the present invention.

FIG. 11(*a*) shows a case where the inspection target solution 212 is sufficiently applied to the application part 81. The applied inspection target solution 212 is developed on the chromatography test strip 8 over the marker reagent hold part 82, the upstream base part 84*a*, the detection part 83, and the downstream base part 84*b*, respectively, and reaches an end part that is further downstream of the downstream base part 84*b*.

FIG. 11(*b*) shows a case where the inspection target solution 212 applied to the application part 81 is insufficient. The applied inspection target solution 212 does not reach the end part downstream of the downstream base part 84*b*.

Then, an optical beam is applied to the end part downstream of the downstream base part 84*b*, and a value of a detection signal obtained in that case is judged. Further, in order to measure the concentration of an analysis target, the same optical beam as the optical beam 211 that is scanned in the vicinity of the detection part 83 is further scanned down to the end part downstream of the downstream base part 84*b*.

As described above, according to the chromatography quantitative measuring apparatus of the ninth embodiment, a deficiency in the amount of inspection target solution applied, and an insufficient development on the chromatography test strip 8 are judged from the detection signal obtained by applying the optical beam to the end part downstream of the downstream base part 84*b* on the chromatography test strip 8 where the inspection target solution is applied. Therefore, it is possible to detect a deficiency in the amount of the inspection target solution 212 applied to the chromatography test strip 8, and an insufficient development on the chromatography test strip 8 which is generated by clogging or the like.

Further, since the optical beam as is scanned down to the end part that is downstream of the base part 84 on the chromatography test strip 8, no new light source is required to detect a deficiency in the amount of inspection target solution applied and an insufficient development on the chromatography test strip 8, thereby restraining increase in the size and cost of the apparatus that accompany addition of the function.

Tenth Embodiment

Hereinafter, a chromatography quantitative measuring apparatus that corresponds to the invention defined in the above-described twenty-ninth aspect of the present invention will be described as a tenth embodiment with reference to FIGS. 12(*a*) and 12(*b*).

Figure 12:
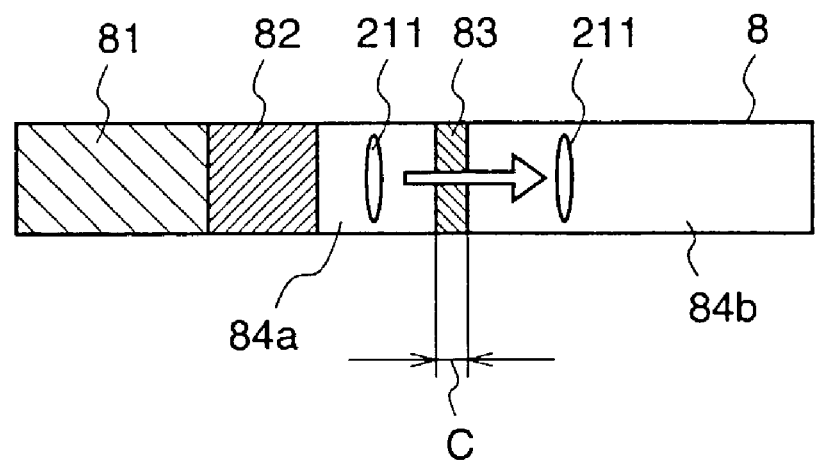
FIGS. 12(a) and 12(b) are diagrams illustrating a measurement of a difference in absorbance on a chromatography test strip according to a tenth embodiment.
Figure 12:
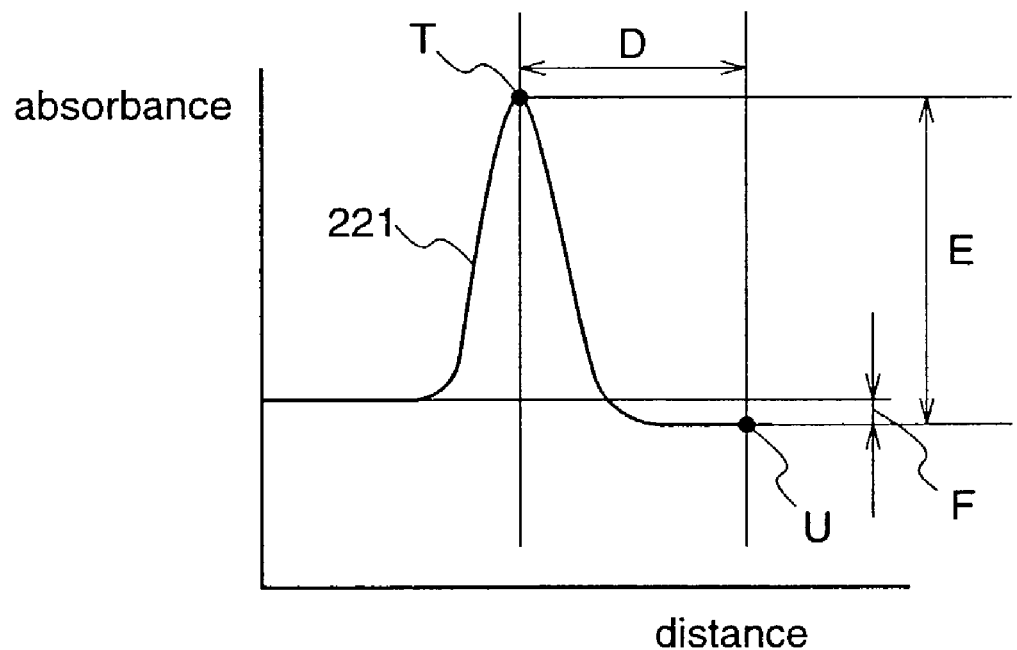

FIGS. 12(*a*) and 12(*b*) are diagrams illustrating a measurement of absorbance on a chromatography test strip according to the tenth embodiment of the present invention. FIG. 12(*a*) illustrates a state of scanning an optical on the chromatography test strip 8, and FIG. 12(*b*) shows a variation of an absorbance signal with respect to the position of the optical beam.

On the chromatography test strip 8, the optical beam 211 is scanned down to the downstream base part 84*b*, after passing through the detection part 83 from the upstream base part 84*a*.

With a value of absorbance at a position where the influence of absorbance of a marker reagent immobilized at the detection part 83 is not exerted, that is, a position U, which is downstream of a position T where the absorbance signal 221 has a peak value, by a distance D, as a standard, the absorbance corresponding to the concentration of an analysis target is obtained as a value E, which is a between the value of absorbance at the position U and the value of absorbance at the peak position T at that time. In other words, although the value of absorbance at the peak position T includes absorption components of the inspection target solution itself, which produces an error in a measurement of the absorbance of the marker reagent immobilized at the detection part 83, an influence of this error can be removed by taking the value of absorbance at the position U (which corresponds to the absorption components of the inspection target solution itself) as a standard. Further, since the standard position is the position U that is not upstream but downstream of the detection part 83, it is possible to remove an error (F in FIG. 12(*b*)) in a measurement of the absorbance, which is due to a marker reagent liable to remain at the upstream base part 84*a*.

As described above, according to the chromatography test strip of the tenth embodiment, when a detection signal at a position which is downstream of the detection part 83 on the chromatography test strip 8 in the direction in which the inspection target solution is developed, where influence of the detection part 83 is not exerted, is a standard value, the detection signal at the detection part 83 is a signal for detecting the concentration to be measured. Therefore, it is possible to reduce an influence of an error in a measurement of the absorbance, which is due to a marker reagent liable to remain at the base part 84*a* upstream of the detection part 83 as compared with the base part 84*b* downstream thereof.

Eleventh Embodiment

Hereinafter, a chromatography quantitative measuring apparatus that corresponds to the invention defined in the above-described thirtieth and thirty-first aspects of the present invention will be described as an eleventh embodiment with reference to FIGS. 13(*a*) and 13(*b*).

Figure 13:
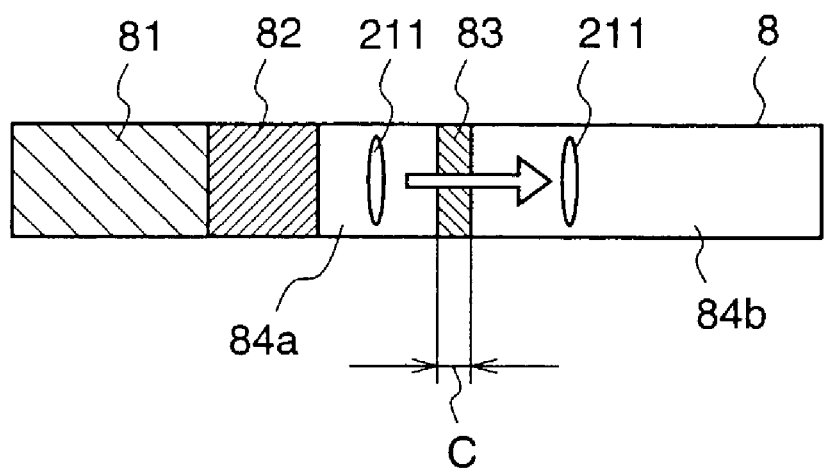
FIGS. 13(a) and 13(b) are diagrams illustrating an electrical noise of an absorbance signal on a chromatography test strip according to an eleventh embodiment.
Figure 13:
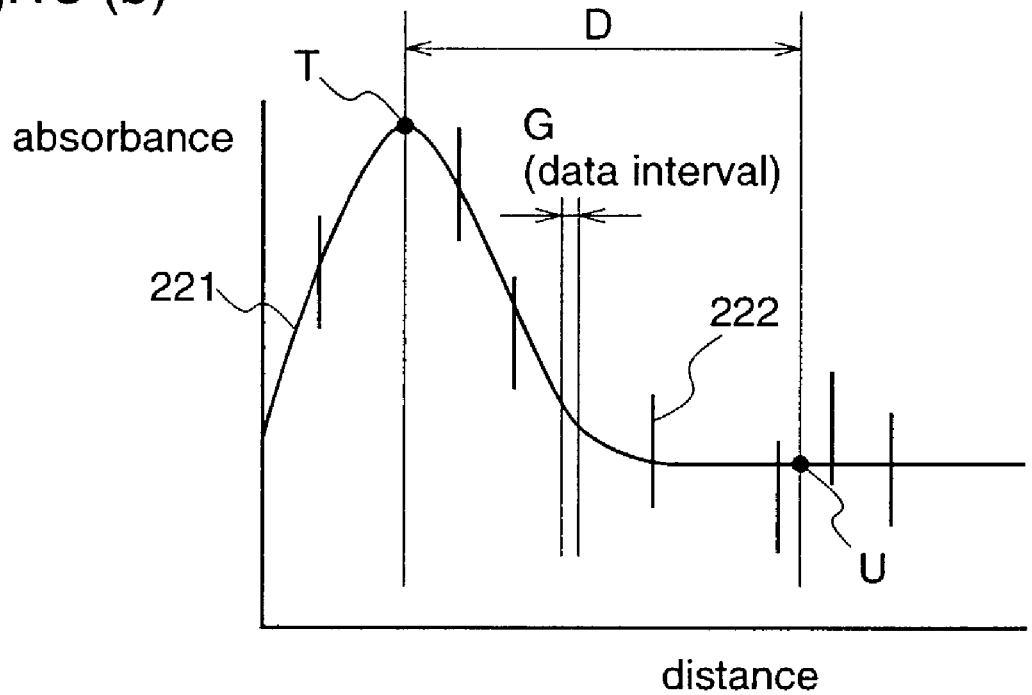

FIGS. 13(*a*) and 13(*b*) are diagrams illustrating a measurement of absorbance on a chromatography test strip according to the eleventh embodiment of the present invention. FIG. 13(*a*) illustrates a state of scanning of an optical beam on the chromatography test strip 8, and FIG. 13(*b*) illustrates a state where a sharp electrical noise 222 is added to a variation of absorbance signal with respect to the position of the optical beam.

On the chromatography test strip 8, the optical beam 211 is scanned down to the downstream base part 84*b*, after passing through the detection part 83 from the upstream base part 84*a*. At this time, data of the absorbance signal 221 is stored at intervals G in which a smooth variation is sufficiently detected.

The electrical noise 222 added to the absorbance signal 221 is generated from a power (such as a switching power) applied to an electric circuit, or a circuit for performing digital processing, and indicates a considerably sharp variation as compared with a scanning speed of the optical beam 211.

When values at the peak position T of the absorbance signal 221 and at the position U, which is downstream of the position T by the distance D, are to be obtained, average values of several data in the vicinity of the respective positions are applied thereto. Further, when the values at the peak position T of the absorbance signal 221 and at the position U, which is downstream of the position T by the distance D, are to be obtained, intermediate values (values of data that are located in the middle of respective data arranged in the order of size) of several data in the vicinity of the respective positions are applied thereto.

Further, the number of data for obtaining the above-described average values and intermediate values are defined within a range so that the reading of the smooth variation of the absorbance signal 221 is not disturbed.

As described above, according to the chromatography quantitative measuring apparatus of the eleventh embodiment, the detection signal at the detection part 83 has an average value of values about an extreme value, and a detection signal as a standard value has an average value of values in the vicinity of a position downstream of the detection part 83 in the direction in which the inspection target solution is developed, where an influence of the detection part 83 is not exerted. Therefore, even when the electrical noise 222 is accidentally added to the detection signal, an influence on the result of calculation for obtaining the concentration of an analysis target can be reduced.

Further, the detection signal at the detection part 83 has an intermediate value of values about an extreme value, and the detection signal as a standard has an intermediate value of values in the vicinity of a position downstream of the detection part 83 in the direction in which the inspection target solution is developed, where an influence of the detection part 83 is not exerted. Therefore, even when the electrical noise 222 is accidentally added to the detection signal, an influence on the result of calculation for obtaining the concentration of an analysis target can be further reduced as compared with the case where the average value is employed.

Twelfth Embodiment

Figure 14:
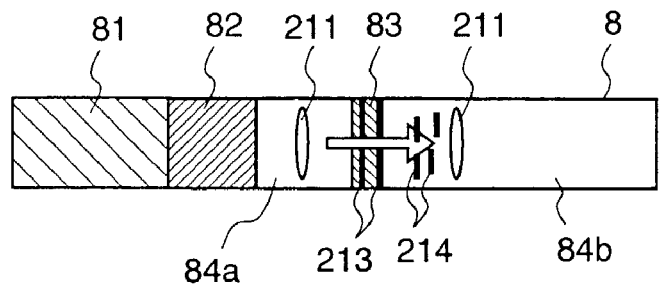
FIGS. 14(a)-14(c) are diagrams illustrating an optical noise of an absorbance signal on a chromatography test strip according to a twelfth embodiment.
Figure 14:
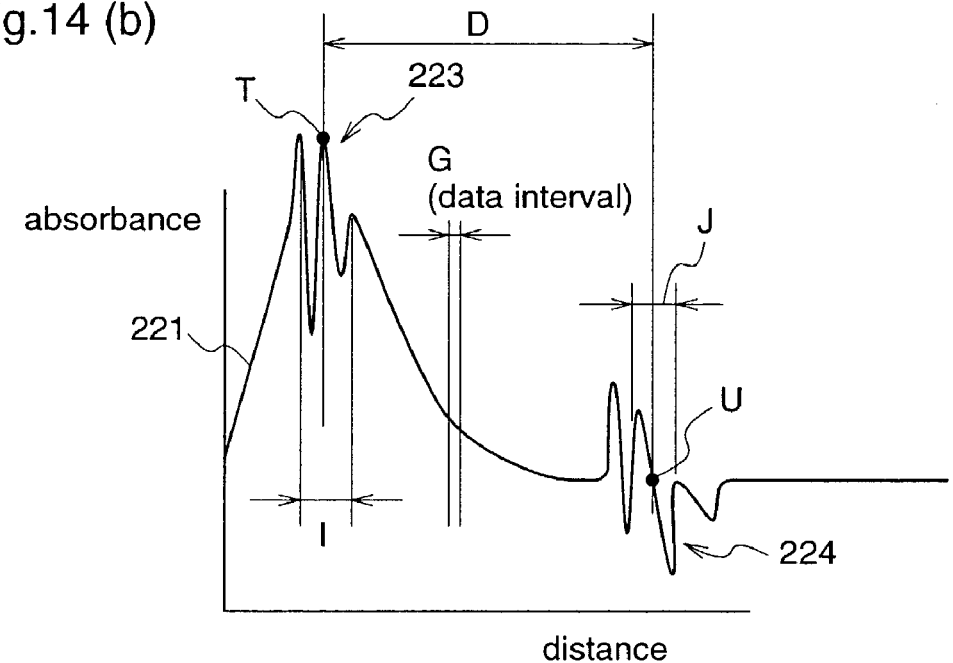
Figure 14:
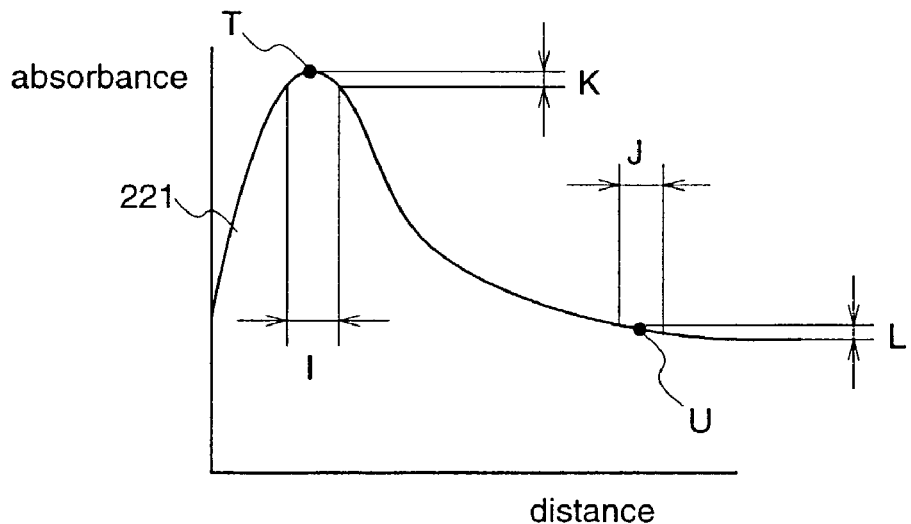

Hereinafter, a chromatography quantitative measuring apparatus that corresponds to the invention defined in the above-described thirty-second and thirty-third aspects of the present invention will be described as a twelfth embodiment with reference to FIGS. 14(*a*)-14(*c*).

FIGS. 14(a)-14(c) are diagrams illustrating a measurement of absorbance on the chromatography test strip 8 according to the twelfth embodiment of the present invention. FIG. 14(a) illustrates a state of scanning of an optical beam on the chromatography test strip 8, and FIG. 14(b) illustrates a state where optical noises 223 and 224 are added to a variation of absorbance signal with respect to the position of the optical beam. FIG. 14(c) shows a normal variation of absorbance signal with respect to the position of the optical beam.

On the chromatography test strip 8, the optical beam 211 is scanned down to the downstream base part 84b, after passing through the detection part 83 from the upstream base part 84a. At this time, data of the absorbance signal 221 is stored at intervals G in which a smooth variation is sufficiently detected. Further, there are obtained an amount K of variation of the absorbance signal 221, which is previously measured on the normal chromatography test strip 8, in the vicinity of the peak position T (interval I), and an amount L of variation of the absorbance signal 221 in the vicinity of the downstream position U (interval J), and values of K+α and L+α (α is tolerance for noise components) are stored as discrimination values at the respective positions.

The optical noises 223 and 224 added to the absorbance signal are generated by non-uniform immobilization of a marker reagent (alias, non-uniform coloration) at the detection part 83, non-uniform development of the marker reagent due to clogging at the downstream base part 84, a flaw on the surface of the chromatography test strip 8, or the like. The optical noises 223 and 224 disturb a smooth variation of the absorbance signal 221, and make a normal measurement of the absorbance impossible according to the noise level.

Then, a comparison is made of values in the vicinity of the peak position T (interval I) of the absorbance signal 221, and when the difference between the maximum value and the minimum value exceeds the discrimination value, the chromatography test strip 8 is judged to be low in performance. Further, a comparison is made of values in the vicinity of the position U, which is downstream of the peak position T of the absorbance signal 221 by the distance D (interval J), and when the difference between the maximum value and the minimum value exceeds the discrimination value, the chromatography test strip 8 is judged to be low in performance.

As described above, according to the chromatography quantitative measuring apparatus of the twelfth embodiment, a comparison is made of the values about the extreme value of the detection signal, and when the difference therebetween exceeds the discrimination value, the chromatography test strip 8 is judged to be low in performance. Therefore, it is possible to avoid an erroneous measurement due to non-uniform immobilization of the marker reagent at the detection part 83, a flaw on the surface of the chromatography test strip 8, or the like.

Further, a comparison is made of the values in the vicinity of the position downstream of the detection part 83 on the chromatography test strip 8 in the direction of development, where an influence of the detection part 83 is not exerted, and when the difference therebetween exceeds the discrimination value, the chromatography test strip 8 is judged to be low in performance. Therefore, it is possible to avoid an erroneous measurement due to non-uniform development of the inspection target solution by clogging at the base part 84, a flaw on the surface of the chromatography test strip 8, or the like.

Thirteenth Embodiment

Hereinafter, a chromatography quantitative measuring apparatus that corresponds to the invention defined in the above-described thirty-fourth to thirty-seventh aspects of the present invention will be described as a thirteenth embodiment with reference to FIG. 15.

Figure 15:
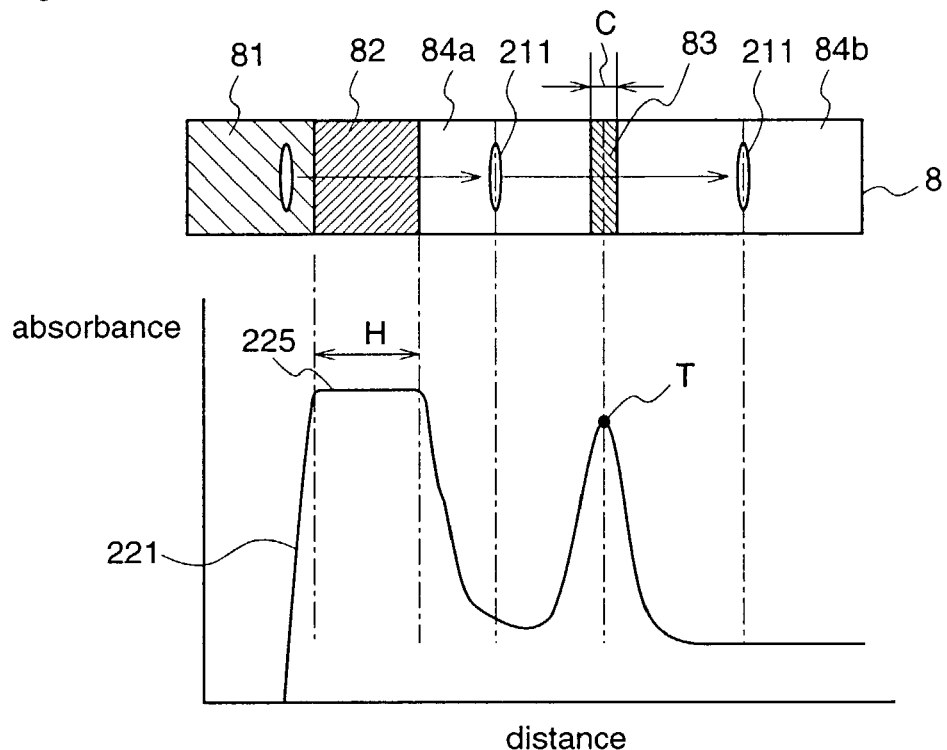
FIG. 15 is a diagram illustrating absorbance on a chromatography test strip including absorbance at a marker reagent hold part, according to a thirteenth embodiment.

FIG. 15 illustrates a state of scanning of an optical beam on the chromatography test strip 8 according to the thirteenth embodiment of the present invention, as well as a variation of an absorbance signal with respect to the position of the optical beam.

A marker reagent remains at the marker reagent hold part 82 even after it is passed by an inspection target solution.

Accordingly, in a measurement of a low-level analysis target, when the optical beam 211 is scanned from a position upstream of the marker reagent hold part 82, there are cases where the absorbance of the marker reagent remaining at the marker regent hold part 82 has a place in the peak position. Further, since the residual marker reagent at the marker reagent hold part 82 is uniformly distributed, an absorbance signal 225 in this region is a flat signal.

Then, in order to avoid an erroneous recognition of the peak position, the optical beam 211 is scanned from the position of the upstream base part 84a excluding the marker reagent hold part 82, and a measurement is started. Alternatively, the flat absorbance signal 225 is detected and discriminated from the absorbance at the peak position T which corresponds to the detection part 83.

Further, a width H of the marker reagent hold part 83 is obtained from the width of the flat absorbance signal 225, and the obtained width H is compared with a prescribed width. Further, a value of the flat absorbance signal 225 is detected, and the amount of residual marker reagent is obtained.

As described above, according to the chromatography quantitative measuring apparatus of the thirteenth embodiment, at a measurement of the concentration, since a measurement is performed on the chromatography test strip 8 exclusive of the marker reagent hold part 82, a measurement value of absorbance at the marker reagent hold part 82 is not included, whereby no erroneous recognition of the absorbance peak position occurs, resulting in a normal detection of the concentration of an analysis target.

Further, the region on the chromatography test strip 8 where the value of the detection signal is flat is taken as the region of the marker reagent hold part 82, whereby no erroneous recognition of the absorbance peak position occurs, resulting in a normal detection of the concentration of an analysis target.

Further, the width of the region on the chromatography test strip 8 where the value of the detection signal is flat is calculated, and the calculated width is compared with a prescribed width of the marker reagent hold part 82, so that the amount of marker reagent held can be confirmed, whereby it is possible to judge whether or not the chromatography test strip 8 is low in performance.

Further, the value in the region on the chromatography test strip 8 where the detection signal is flat is detected, and the amount of residual marker reagent is confirmed from the value, whereby it is possible to confirm whether or not the marker reagent has flown normally.

Fourteenth Embodiment

Hereinafter, a chromatography quantitative measuring apparatus that corresponds to the invention defined in the above-described thirty-eighth and thirty-ninth aspects of the present invention will be described as a fourteenth embodiment with reference to FIG. 16.

Figure 16:
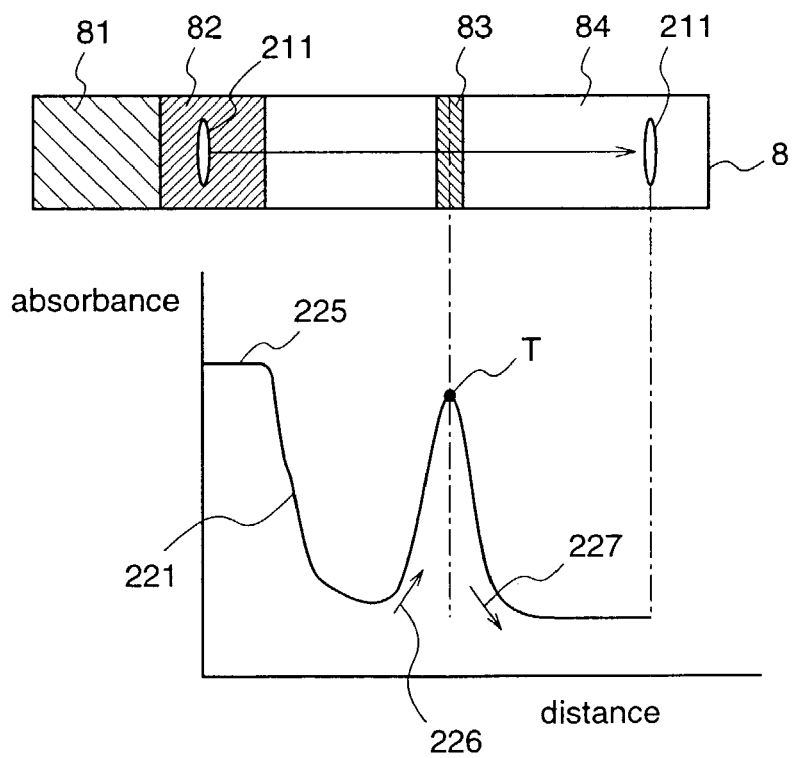
FIG. 16 is a diagram illustrating a method for detecting a peak value of absorbance on a chromatography test strip according to a fourteenth embodiment.

FIG. 16 illustrates a state of scanning of an optical beam on the chromatography test strip 8 according to the fourteenth embodiment of the present invention, as well as a variation of an absorbance signal 221 with respect to the position of the optical beam.

A marker reagent remains at the marker reagent hold part 82 even after it is passed by an inspection target solution. Accordingly, in a measurement of a low-level analysis target, when the optical beam 211 is scanned from the position of the marker reagent hold part 82, there are cases where the absorbance of the marker reagent remaining at the marker regent hold part 82 has a place in the peak position.

Then, a rise part 226 and a fall part 227 are detected from a variation in inclination of the absorbance signal 211, and the maximum position in an area between the rise part 226 and the fall part 227 is recognized as the peak position T.

Further, an interval between the rise part 226 and the fall part 227 is obtained, and the obtained interval is compared with a prescribed width of the detection part 83.

As described above, according to the chromatography quantitative measuring apparatus of the fourteenth embodiment, the rise part 226 and the fall part 227 of the detection signal are recognized, and the extreme value of the detection signal is obtained, whereby no erroneous recognition of the absorbance peak position occurs, resulting in a normal detection of the concentration of an analysis target.

Further, the rise part 226 and the fall part 227 of the detection signal are recognized, an interval between the rise part 226 and the fall part 227 is calculated, and the size of the interval is compared with a prescribed width of the detection part 83, thereby confirming the width of the detection part 83. Therefore, it is possible to judge whether or not the chromatography test strip is low in performance.

Fifteenth Embodiment

Hereinafter, a chromatography quantitative measuring apparatus that corresponds to the invention defined in the above-described fortieth to forty-third aspects of the present invention will be described as a fifteenth embodiment with reference to FIG. 17.

Figure 17:
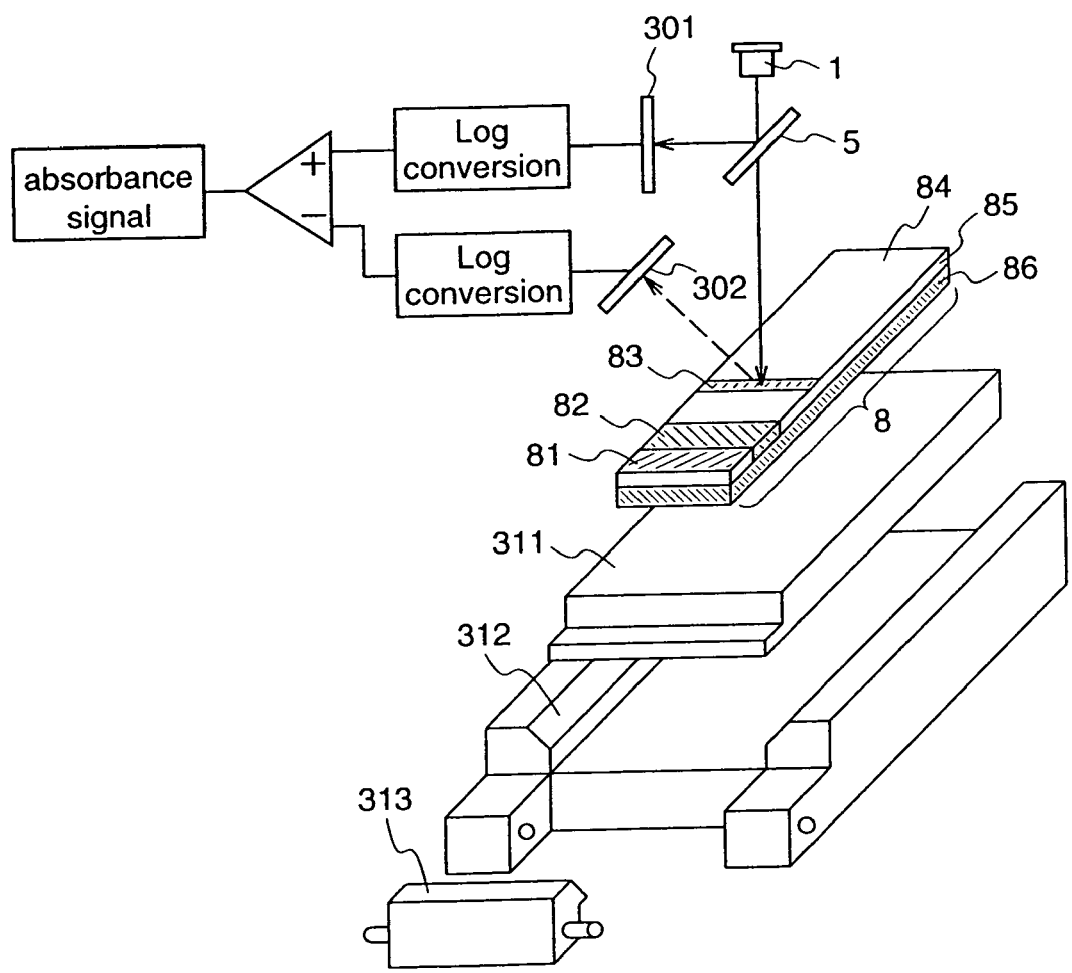
FIG. 17 is a perspective view of a chromatography measuring apparatus according to a fifteenth embodiment.

FIG. 17 is a perspective view of the chromatography quantitative measuring apparatus according to the fifteenth embodiment.

In FIG. 17, reference numeral 1 denotes a light source, which emits a beam. Reference numeral 5 denotes a glass plate. Reference numeral 301 denotes a light receiving element, which receives a beam reflected at the glass plate 5. Reference numeral 302 denotes a light receiving element, which receives a beam that is transmitted through the glass plate 5 and reflected at the detection part 83 of an immuno-chromatography test strip 8. Reference numeral 8 denotes the immuno-chromatography test strip, which comprises a development layer 85 where an applied inspection target solution permeates and a carrier 86 that holds the development layer 85, and is approximately 50 mm long by 5 mm wide.

The development layer 85 comprises an application part 81 where the inspection target solution is applied, a marker reagent hold part 82 which has a marker reagent that specifically causes a binding reaction with a measurement target included in the inspection target solution, a detection part 83 which has a reagent for immobilizing a specifically bounded material of the measurement target and the marker reagent, and a base part 84 which is located at a prescribed distance from the detection part 83 in order to avoid the occurrence of an error in an absorbance signal due to the bounded material that is not immobilized at the detection part 83. The development layer 85 is made of a membrane filter as a material that can be penetrated by the inspection target solution. In addition to the membrane filter, any arbitrary materials which can be penetrated by the inspection target solution, such as glass fiber filter paper and a nonwoven fabric, can be employed as a material used for the development layer 85.

The carrier 86 is made of a PET (Polyethylene terephthalate) as a material which is not permeated by the inspection target solution. In addition to the PET, any arbitrary material which is not penetrated by the inspection target solution, such as an ABS, can be employed as a material used for the carrier 86. By dropping an inspection target solution to the so-constituted immuno-chromatography test strip 8, a measurement target included in the inspection target solution can be measured.

Reference numeral 311 denotes a fixing table, which holds the immuno-chromatography test strip 8. The fixing table 311 can be used repeatedly at a quantitative measurement, and the immuno-chromatography test strip 8 can be reattached thereto after a quantitative measurement. Thus, there is no necessity of a conventional hard case, thereby reducing the cost and minimizing a storage space for components required for the quantitative measurement.

Reference numeral 312 denotes a measurement table, which holds the fixing table 311. At this time, the measurement table 312 is provided with a groove for positioning the fixing table 311. Thereby, the fixing table 311 can be accurately attached to the measurement table 312. Further, by constructing the measurement table 312 so that it can be scanned, a quantitative measurement is performed by scanning a beam in the area down to the detection part 83 and the base part 84. Thereby, the absorbance signal at the detection part 83 and the base part 84 can be obtained. Here, the beam applied to the immuno-chromatography test strip 8 may be shaped circularly, elliptically, or rectangularly. Further, it is desirable that the beam is shaped so as to be applied to the whole detection part 83.

Reference numeral 313 denotes a fixing table carrier, which is movably attached to the measurement table 312 and employed to fix the fixing table 311 on the measurement table 312.

A description will be given of a quantitative measurement on the chromatography test strip 8 employing the so-configured chromatography quantitative measuring apparatus.

First, an inspection target solution is applied to the application part 81 of the immuno-chromatography test strip 8. The applied inspection target solution is developed on the development layer 85. When a measurement target is included in the applied inspection target solution, at the marker reagent hold part 82, the measurement target included in the inspection target solution specifically causes a binding reaction with a marker reagent held at the marker reagent hold part 82. Then, the measurement target specifically bonded to the marker reagent, that is, a bounded material, is immobilized at the detection part 83. At this time, a discoloring reaction is caused with a width of approximately 1 mm. The concentration at a discoloration part and the concentration of the measurement target are in proportion. The inspection target solution passing through the detection part 83 permeates the development layer 85 to be absorbed therein.

When the development of the inspection target solution is completed, a beam is emitted from the light source 1, and the emitted beam is input to the glass plate 5. The beam reflected at the glass plate 5 is input to the light receiving element 301 as a reference beam. On the other hand, the beam transmitted through the glass plate 5 is applied to the immuno-chromatography test strip 8. At this time, a scattering light generated on the surface of the development layer 85 is detected by the light receiving element 302. Then, the reference beam and the scattering light detected by the light receiving element 301 and the light receiving element 302 are respectively subjected to Log transformation, and the result of subtraction with these Log transformed values is obtained as an absorbance signal.

As described above, according to the chromatography quantitative measuring apparatus of the fifteenth embodiment, a measurement operation can be performed without the inspection target solution adhering to the chromatography quantitative measuring apparatus, and the immuno-chromatography test strip 8 can be easily attached to the chromatography quantitative measuring apparatus. Further, the beam can be accurately applied to the area down to the detection part 83 and the base part 84. Furthermore, a measurement can be performed solely with the immuno-chromatography test strip 8, so that there is no need to put the chromatography test strip 8 in a case individually, thereby reducing the cost for the casing and minimizing a storage space.

Sixteenth Embodiment

Hereinafter, a chromatography quantitative measuring apparatus that corresponds to the invention defined in the above-described forty-forth to fifty-third aspects of the present invention will be described as a sixteenth embodiment with reference to FIG. 18.

The difference from the fifteenth embodiment is that the carrier 86 and the fixing table 311 are provided with a hole 320 and a projection 321, respectively, so that the immuno-chromatography test strip 8 can be easily and more accurately attached to the fixing table 311. The quantitative measuring method with the immuno-chromatography test strip 8 has been described with respect to the fifteenth embodiment, and a description thereof will be omitted here.

Figure 18:
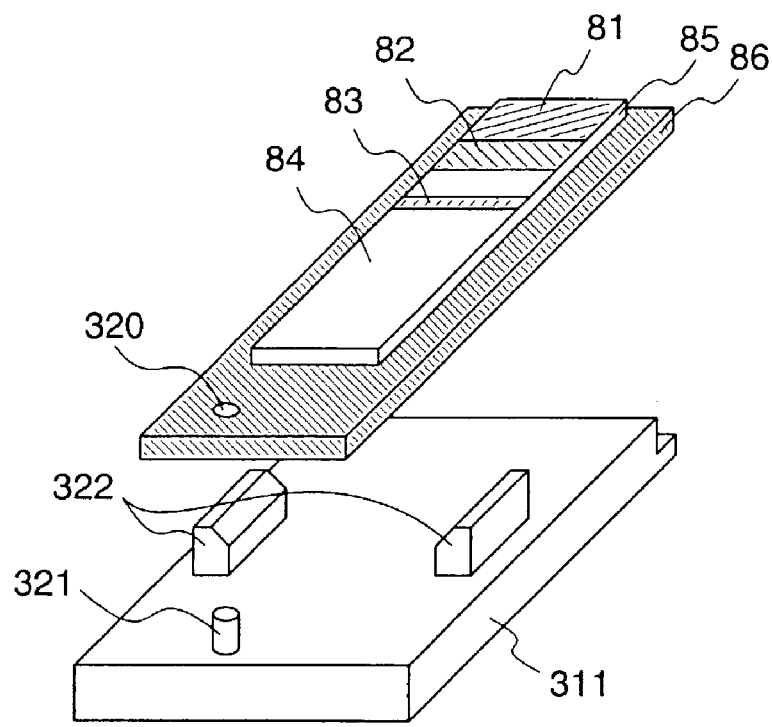
FIG. 18 is a perspective view of a chromatography quantitative measuring apparatus according to a sixteenth embodiment.

FIG. 18 is a perspective view of the chromatography quantitative measuring apparatus according to the sixteenth embodiment. In FIG. 18, the same or corresponding constituent elements as those shown in FIG. 17 are denoted by the same reference numerals, and descriptions thereof will be omitted.

In FIG. 18, reference numeral 320 denotes the hole, which is provided in the carrier 86 of the immuno-chromatography test strip 8. While the hole 320 has a round shape, the hole 320 may have a rectangular shape. When the hole 320 has a rectangular shape, a side or plural sides of the rectangle is employed for positioning of the immuno-chromatography test strip 8, so that the immuno-chromatography test strip 8 can be attached to the fixing table 311 more accurately. Further, when the hole 320 is provided in the carrier 86 at a position downstream in the direction in which the inspection target solution is developed, the inspection target solution is prevented from adhering to the hole 320 and the projection 321 during application of the inspection target solution. Furthermore, when the hole 320 is provided asymmetrically with respect to the center line of the immuno-chromatography test strip 8 in the longer-side direction, the immuno-chromatography test strip 8 is prevented from being erroneously attached to the fixing table 311 inside out.

Figure 19:
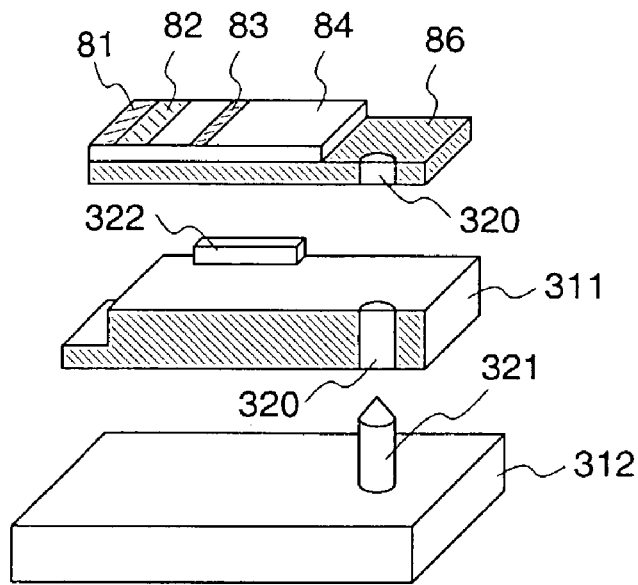
FIG. 19 is a cross sectional view of a chromatography quantitative measuring apparatus which is provided with a projection on a measurement table and holes in a carrier and a fixing table, in which the projection can be inserted.

Reference numeral 321 denotes the projection, which is provided on the fixing table 311 in the shape same as that of the hole 320 or a shape having a diameter slightly smaller than the that of the hole 320. This projection 321 may be provided on the measurement table 312. In this case, as shown in FIG. 19, a hole with the shape same as that of the hole 320 is provided in the fixing table 311, and the projection 321 provided on the measurement table 312 penetrates the holes in the fixing table 311 and the carrier 86, so that the immuno-chromatography test strip 8 is easily attached to the fixing table 311 and accurately attached to the measurement table 312. At this time, it is desirable that the end of the projection 321 is inclined.

Reference numeral 322 denotes a guide for positioning the carrier 86, which is provided on the fixing table 311. The guide 322 is the same in width as the carrier 86 or slightly wider than the carrier 86. The immuno-chromatography test strip 8 is held on the fixing table 311 with the carrier 86 following the shape of the guide 322. Here, when the carrier 86 is larger than the development layer 85, it is the carrier 86 that contacts with the guide 322, whereby the development layer 85 is prevented from being stripped off and adhering to the guide 322 in a detachment operation. Further, when the end faces of the guide 322 are inclined, the immuno-chromatography test strip 8 is easily attached to the fixing table 311.

As described above, according to the chromatography measuring device of the sixteenth embodiment, the carrier 86 is larger than the development layer 85, so that it is the carrier 86 that contacts with the guide 322, whereby it is possible to prevent the development layer 85 from being stripped off and adhering to the guide 322 in a detachment operation.

Further, the hole 320 is provided in the carrier 86 at a position downstream in the direction in which the inspection target solution is developed, and the projection 321 with the shape approximately the same as that of the hole 320 and the guide 322 for fixing the carrier 86 are provided on the fixing table 311. Therefore, the development layer 85 is prevented from being stripped off and adhering to the projection 321. Further, the inspection target solution is prevented from adhering to the hole 320 and the projection 321 during application of the inspection target solution, whereby even when the immuno-chromatography test strip 8 is repeatedly attached to the fixing table 311, the accuracy of attachment is not deteriorated, and the immuno-chromatography test strip 8 can be easily and accurately attached to the fixing table 311.

In the sixteenth embodiment, when a notch is also provided in the carrier 86, and the shape of the guide 322 is the same as that of the notch provided in the carrier 86, so that the guide 322 is inserted in the notch, the immuno-chromatography test strip 8 can be accurately attached to the fixing table 311. At this time, when the notch is provided asymmetrically with respect to the center line of the immuno-chromatography test strip 8 in the longer-side direction, or the notch and the guide 322 are provided only on one side, the immuno-chromatography test strip 8 is prevented from being attached to the fixing table 311 inside out.

Seventeenth Embodiment

Hereinafter, a chromatography quantitative measuring apparatus that corresponds to the invention defined in the above-described fifty-fourth to sixty-second aspects of the present invention will be described as a seventeenth embodiment with reference to FIG. 20.

The difference from the sixteenth embodiment is that a test strip fixing device 323 that can be attached to the fixing table 311 is provided. The quantitative measurement on the immuno-chromatography test strip 8 has been described with respect to the fifteenth embodiment, and a description thereof will be omitted here.

Figure 20:
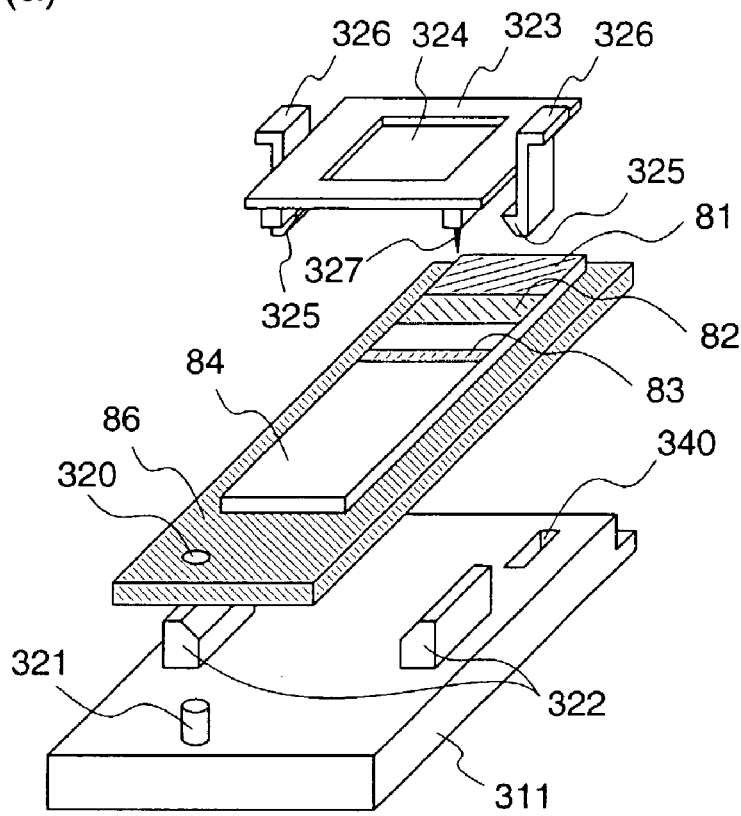
FIGS. 20(a) and 20(b) are perspective views of a chromatography quantitative measuring apparatus according to a seventeenth embodiment.
Figure 20:
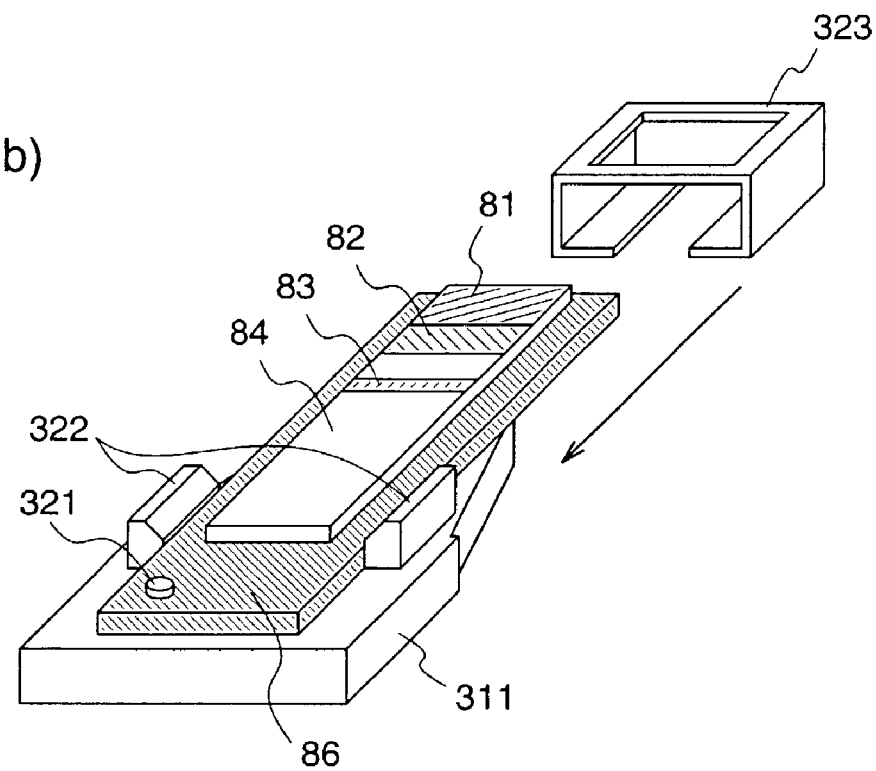

FIGS. 20(*a*) and 20(*b*) are perspective views of the chromatography quantitative measuring apparatus according to the seventeenth embodiment. In FIGS. 20(*a*) and 20(*b*), the same or corresponding constituent elements as those shown in FIG. 18 are denoted by the same reference numerals, and descriptions thereof will be omitted.

In FIG. 20(a), reference numeral 323 denotes the test strip fixing device, which presses a measurement area of the immuno-chromatography test strip 8 to smooth a part where a beam is applied, when the immuno-chromatography test strip 8 is attached to the fixing table 311. Here, an area of the carrier 86 where the beam is scanned is pressed. Thereby, the development layer 85 is prevented from adhering to the test strip fixing device 323, and thus, the accuracy of attachment of the test strip fixing device 323 can be maintained even when attachment and detachment thereof is repeated. It is desirable that a part that contacts with the carrier 86 has elasticity. While the test strip fixing device 323 and the fixing table 311 are different components, the test strip fixing device 323 may be integrated with the fixing table 311. By this configuration, it is possible to prevent a loss of the test strip fixing device 323.

Reference numeral 324 denotes a transmission window, through which a beam is transmitted. The transmission window 324 is provided on the surface of the test strip fixing device 323 where the beam is applied, is slightly wider than the width of the beam, and is long enough in the longer-side direction not to prevent the beam from being scanned. Therefore, a measurement of absorbance can be performed while the test strip fixing device 323 is attached.

Reference numeral 325 denotes a pawl-shaped projection, which is provided in the test strip fixing device 323 to fix the test strip fixing device 323 on the fixing table 311. While a hole 340 in which the pawl-shaped projection 325 is inserted is provided in the fixing table 311, it is also possible that an interval between the two pawl-shaped projections 325 are made equal to the width of the fixing table 311, so that the test strip fixing device 323 is fixed.

Reference numeral 326 denotes a handle, which is provided in the test strip fixing device 323 to make it easy to attach/detach the test strip fixing device 323 to/from the fixing table 311. It is desired that the handle 326 has a shape which is easy for an operator to hold when he/she attaches/detaches the test strip fixing device 323 to/from the fixing table 311, and it is more desirable that the surface of the handle 326 is subjected to anti-slipping processing.

Reference numeral 327 denotes a needle, which is provided in the test strip fixing device 323. When the test strip fixing device 323 is attached to the fixing table 311, the needle 327 penetrates the chromatography test strip 8, here, the carrier 86. Therefore, when the test strip fixing device 323 is detached from the fixing table 311, the immuno-chromatography test strip 8 is detached from the fixing table 311 with the test strip fixing device 323, whereby the immuno-chromatography test strip 8 can be disposed of without an inspection target solution adhering to an operator.

As described above, according to the chromatography quantitative measuring apparatus of the seventeenth embodiment, the immuno-chromatography test strip 8 is attached to the fixing table 311, and the test strip fixing device 323 having the transmission window 324 is attached thereto. Therefore, the area where the beam is scanned is smoothed, so that the accuracy of a measurement of absorbance is enhanced, and the measurement of absorbance can be performed while the test strip fixing device 323 is attached.

Further, by bringing the test strip fixing device 323 into contact with the carrier 86, the development layer 85 is prevented from adhering to the test strip fixing device 323, and thus, the accuracy of attachment of the test strip fixing device 323 can be maintained even when attachment and detachment thereof is repeated.

Furthermore, since the needle 327 is provided in the test strip fixing device 323, the immuno-chromatography test strip 8 is detached from the fixing table 311 with the test strip fixing device 323 when the test strip fixing device 323 is detached from the fixing table 311, whereby it is possible to dispose of the immuno-chromatography test strip 8 without an inspection target solution adhering to an operator.

While in the seventeenth embodiment a description has been given of the case where the test strip fixing device 323 is attached to the fixing table 311 employing the pawl-shaped projections 325 as shown in FIG. 20(a), the test strip fixing device 323 may be attached to the fixing table 311 by sliding the test strip fixing device 323 along the fixing table 311, as shown in FIG. 20(b). At this time, the test strip fixing device 323 and the fixing table 311 are fixed by taking the shape of wedge. Further, it is also possible that an inclination part is provided in the test strip fixing device 323 or the fixing table 311, so that the test strip fixing device 323 and the fixing table 311 are brought into contact at this inclination part, thereby fixing the test strip fixing device 323 on the fixing table 311.

Eighteenth Embodiment

Hereinafter, a chromatography quantitative measuring apparatus that corresponds to the invention defined in the above-described sixty-third to sixty-eighth aspects of the present invention will be described as an eighteenth embodiment with reference to FIG. 21.

The difference from the fifteenth embodiment is that the carrier 86 and the fixing table 311 are provided with grooves 328 and a guide 329, respectively. The quantitative measurement on the immuno-chromatography test strip 8 has been described with respect to the fifteenth embodiment, and a description thereof will be omitted here.

Figure 21:
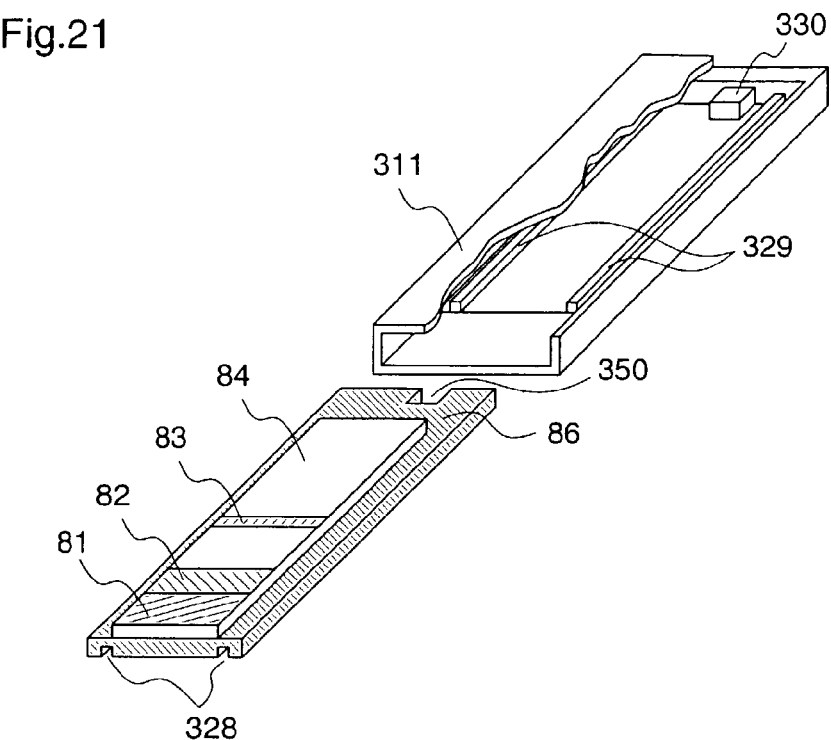
FIG. 21 is a cross sectional view of a chromatography quantitative measuring apparatus according to an eighteenth embodiment.

FIG. 21 is a cross sectional view of the chromatography quantitative measuring apparatus according to the eighteenth embodiment. In FIG. 21, the same or corresponding constituent elements as those shown in FIG. 17 are denoted by the same reference numerals, and descriptions thereof will be omitted.

In FIG. 21, the immuno-chromatography test strip 8 is provided with a notch 350 at its end on the side of insertion into the fixing table 311. When the notch 350 is provided asymmetrically with respect to the center line of the immuno-chromatography test strip 8 in the longer-side direction, it is possible to prevent a failure such as an inside-out attachment of the immuno-chromatography test strip 8.

The carrier 86 is provided with the grooves 328. When the grooves 328 are formed by a laser cutter which is employed when the immuno-chromatography test strip 8 is formed, a process of operation can be omitted. At this time, it is desired that the grooves 328 and the guide 329 are provided asymmetrically with respect to the center line of the immuno-chromatography test strip 8 in the longer-side direction.

The fixing table 311 is provided with a projection 330 having the shape same as that of the notch 350, the guide 329 which can be inserted in the grooves 328, and an insertion slot in which the immuno-chromatography test strip 8 can be inserted. Here, the insertion slot is inclined so as to becomes narrower toward the interior of the fixing table 311.

As described above, according to the chromatography quantitative measuring apparatus of the eighteenth embodiment, the immuno-chromatography test strip 8 can be fixed in the fixing table 311 at a prescribed position. At this time, since the notch 350 provided in the carrier 86 is provided asymmetrically with respect to the center line of the immuno-chromatography test strip 8 in the longer-side direction, the immuno-chromatography test strip 8 can be prevented from being attached inside out.

Nineteenth Embodiment

Hereinafter, a chromatography quantitative measuring apparatus that corresponds to the invention defined in the above-described sixty-ninth to seventy-seventh aspects of the present invention will be described as a nineteenth embodiment with reference to FIGS. 22(*a*) and 22(*b*).

The difference from the fifteenth embodiment is that the carrier 86 and the fixing table 311 are provided with the groove 328 and the guide 329, respectively. The quantitative measurement on the immuno-chromatography test strip 8 has been described with respect to the fifteenth embodiment, and a description thereof will be omitted here.

Figure 22:
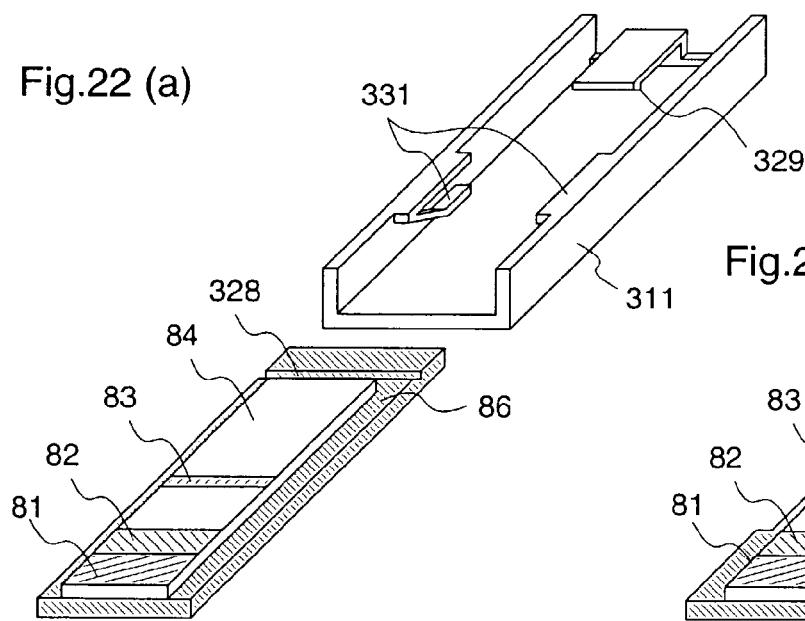
FIGS. 22(a) and 22(b) is a perspective views of a chromatography quantitative measuring apparatus according to a nineteenth embodiment.
Figure 22:
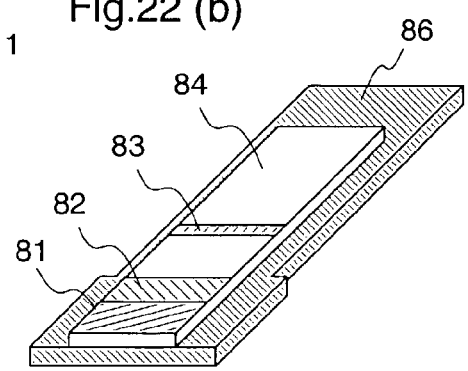

FIGS. 22(*a*) and 22(*b*) are perspective views of the chromatography quantitative measuring apparatus according to the nineteenth embodiment. In FIGS. 22(*a*) and 22(*b*), the same or corresponding constituent elements as those shown in FIG. 21 are denoted by the same reference numerals, and descriptions thereof will be omitted.

In FIG. 22(*a*), the carrier 86 is provided with the groove 328 at its end on the side of insertion into the fixing table 311.

The fixing table 311 is provided with the guide 329 which can be inserted in the groove 328, and a holding member 331 for pressing the immuno-chromatography test strip 8, which is made of an elastic member.

When the immuno-chromatography test strip 8 is completely inserted in the fixing table 311, the guide 329 is inserted in the groove 328, so that the immuno-chromatography test strip 8 is fixed in the fixing table 311 at a prescribed position. At this time, when there is provided a means for detecting the insertion of the guide 329 into the groove 328, it is possible to recognize that the immuno-chromatography test strip 8 is correctly disposed in the fixing table, whereby an erroneous measurement operation can be prevented. As an example, there is a configuration in which the guide 329 is provided with an electrode and the surface of the groove 328 is covered with a conductive material.

The holding member 331 is integrated with the fixing table 311 and presses the vicinity of an area on the immuno-chromatography test strip 8 where a beam is scanned. Specifically, it is desired that a part of the carrier 86 is pressed, and the end of the holding member 331 is inclined. The immuno-chromatography test strip 8 inserted in the fixing table 311 is positioned as the end of the carrier 86 is introduced with walls of the fixing table 311 as a guide. It is desired that there is provided a mechanism for releasing the holding member 331 in a process for removing the immuno-chromatography test strip 8 from the fixing table 311. The holding member 331 may not be necessarily integrated with the fixing table 311 and may be provided in the chromatography quantitative measuring apparatus. In this case, it is desirable that the holding member 331 is detachable.

While the position of the immuno-chromatography test strip 8 is decided by employing the groove 328 and the guide 329 in FIG. 22(*a*), the position may be decided by the carrier 86 whose width on the insertion side is narrowed to form stages, as shown in FIG. 22(*b*).

As described above, according to the chromatography quantitative measuring apparatus of the nineteenth embodiment, since the holding member 331 for pressing the carrier 86 is provided, an area where a beam is scanned can be smoothed, thereby enhancing the accuracy of a measurement of absorbance. At this time, since the end of the holding member 331 is inclined, the holding member 331 is easily attached/detached to/from the fixing table 311.

Twentieth Embodiment

Hereinafter, a chromatography quantitative measuring apparatus that corresponds to the invention defined in the above-described seventy-eighth to eighty-eighth aspects of the present invention will be described as a twentieth embodiment with reference to FIGS. 23 and 24.

The quantitative measurement on the immuno-chromatography test strip 8 has been described with respect to the fifteenth embodiment, and a description thereof will be omitted here.

Figure 23:
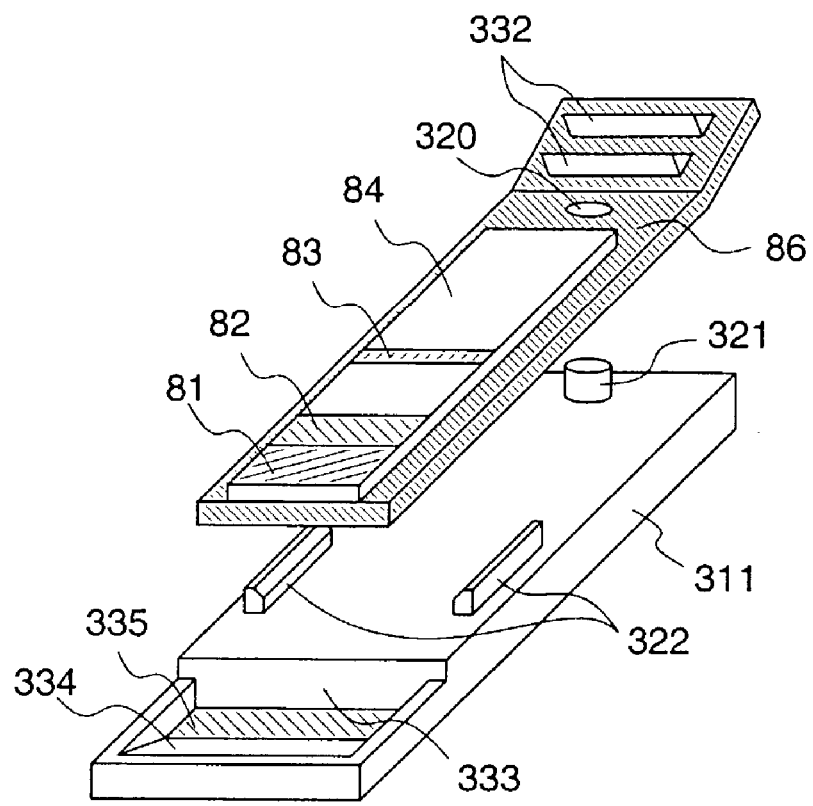
FIG. 23 is a perspective view of a chromatography quantitative measuring apparatus according to a twentieth embodiment.

FIG. 23 is a perspective view of the chromatography quantitative measuring apparatus according to the twentieth embodiment. In FIG. 23, the same or corresponding constituent elements as those shown in FIG. 17 are denoted by the same reference numerals, and descriptions thereof will be omitted.

In FIG. 23, an operator holds the carrier 86 and detaches the immuno-chromatography test strip from the fixing table 311. Thereby, it is possible to prevent the operator from being contaminated with a sample when detaching the immuno-chromatography test strip 8. At this time, as shown in FIG. 23, the carrier 86 is bent and the end thereof is in the air, so that the operator can hold this bent part. At this time, the part of the carrier 86 which is to be held is provided with a slip stopper 332. Therefore, the operator can easily hold the bent part when detaching the immuno-chromatography test strip 8, resulting in an enhancement in operationlity. While the slip stopper 332 is provided in the shape of projections, the slip stopper 332 may take the shape of grooves or shape obtained by a knurling processing on the surface of the carrier 86. Here, when a groove is previously provided at a part where a valley is to be made when the carrier 86 is bent, the carrier 86 can be bent easily, thereby detaching the immuno-chromatography test strip 8 easily. Further, when the part of the carrier 86 which is to be held protrudes above the fixing table 311, the operator can hold the part easily, resulting in an enhancement in operationality.

The fixing table 311 is provided with a saucer 333 which is a groove for receiving an inspection target solution, and an aperture of this saucer 333 is larger than the carrier 86. Further, the saucer 333 is provided with a slope 334, so that the inspection target solution can be applied not only to the application part 81 of the immuno-chromatography test strip 8 from above but also to the development layer 85 from the cross-sectional direction. When the surface of the fixing table 311 is subjected to water repellent finishing, a sample which erroneously escapes during the application of sample to the immuno-chromatography test strip 8 can be easily wiped. Further, since an absorbent material 335 as an absorbent substance is attached to the saucer 333 of the fixing table 311, the sample which erroneously escapes during the application of sample is absorbed by the absorbent material 335, so that the sample is prevented from adhering to the chromatography quantitative measuring apparatus. The absorbent material 335 is provided on the bottom surface of the saucer 333 and is replaceable.

Figure 24:
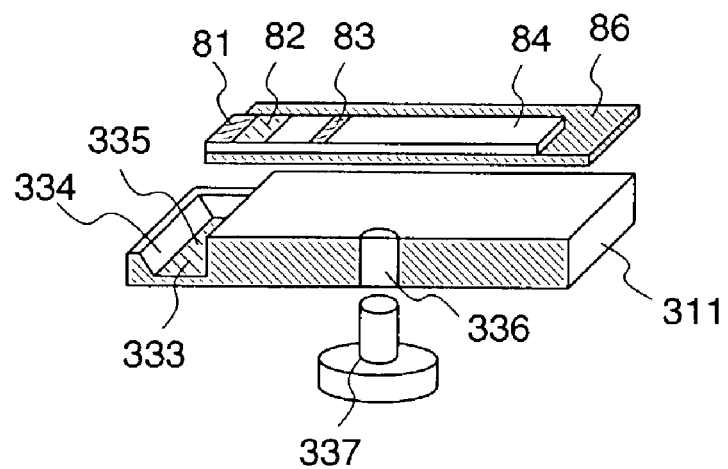
FIG. 24 is a cross sectional view of a chromatography quantitative measuring apparatus which is provided with a through hole in a fixing table, which a removal bar can penetrate.

Further, as shown in FIG. 24, when the fixing table 311 is provided with a through hole 336 at a part that contacts with the carrier 86, so that a removal bar 337 is inserted in the through hole 336, the immuno-chromatography test strip 8 can be easily removed from the fixing table 311. The removal bar 337 may be integrated with the fixing table 311.

As described above, according to the chromatography quantitative measuring apparatus of the twentieth embodiment, it is possible to prevent the inspection target solution from adhering to an operator when the operator detaches the immuno-chromatography test strip 8 on which a measurement is finished from the fixing table 311. Here, since the fixing table 311 is subjected to water repellent finishing, an inspection target solution that erroneously adheres to the fixing table 311 is easily wiped. Further, since the slope 334 is provided, even when a different method of applying the inspection target solution is employed, the fixing table 311 is applicable thereto without being replaced.

APPLICABILITY IN INDUSTRY

A chromatography quantitative measuring apparatus according to the present invention has a high accuracy of a quantitative measurement, and is available as a chromatography quantitative measuring apparatus for a measurement employing an immuno-chromatography test strip or the like.

The invention claimed is:

1. A chromatography quantitative measuring apparatus for applying a beam to a chromatography specimen on which a sample is added, detecting an optical signal from a transmitted light or reflected light from the chromatography specimen, and quantitatively reading a concentration of the sample from the detected optical signal, said apparatus comprising:
   a laser for emitting a beam to the chromatography specimen; and
   an optical mechanism for forming the beam emitted from said laser into an elliptically-shaped beam having an area smaller than a detection area of the chromatography specimen and applying the elliptically-shaped beam to the chromatography specimen such that a long side of the elliptically-shaped beam applied to the chromatography specimen is shorter than a width of the chromatography specimen in a width direction of the chromatography specimen perpendicular to a longitudinal direction of the chromatography specimen, and a short side of the elliptically-shaped beam applied to the chromatography specimen is shorter than a width of the detection area of the chromatography specimen, said optical mechanism comprising:
   a collimator lens for converting the beam emitted from said laser into a collimated beam;
   a circular aperture member for shaping a long side of the collimated beam that has passed through said collimator lens; and
   a cylindrical lens for shaping a short side of the collimated beam that has passed through said aperture member, thereby shaping the collimated beam into an elliptically-shaped beam.

2. The chromatography quantitative measuring apparatus as defined claim 1, further comprising a detector for detecting the optical signal by scanning the elliptically-shaped beam applied to the chromatography specimen, or the chromatography specimen along the longitudinal direction of the specimen, within a range shorter than the width of the chromatography specimen in the width direction of the chromatography specimen.

3. The chromatography quantitative measuring apparatus as defined in claim 1, further comprising
   a compensation device for storing an initial wavelength of said laser, calculating a present wavelength of said laser to compensate for a temperature change detected by a temperature detection element provided in a vicinity of said laser, and compensating an optical signal detection value or a converted concentration of the sample which is obtained by converting the optical signal detection value.

4. The chromatography quantitative measuring apparatus as defined in claim 3, wherein said compensation device performs processing for detecting the optical signal, processing for obtaining the converted concentration of the sample, and processing for compensating the converted concentration with the same calculator.

* * * * *